US011786537B2

(12) United States Patent
Al-Zaydi et al.

(10) Patent No.: US 11,786,537 B2
(45) Date of Patent: Oct. 17, 2023

(54) THERAPEUTIC INHIBITION AFFINITY OF COPPER (II) COMPLEX AND THEIR DIAZENYL PYRIDINONE HETEROCYCLIC LIGANDS AGAINST SARS-COV2

(71) Applicant: King Abdulaziz University, Jeddah (SA)

(72) Inventors: Khadijah M. Al-Zaydi, Jeddah (SA); Mostafa A. Hussien A. Hussein, Jeddah (SA); Ahlam Ibrahim Alsulami, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/670,469

(22) Filed: Feb. 13, 2022

(65) Prior Publication Data

US 2023/0255981 A1 Aug. 17, 2023

(51) Int. Cl.
*A61K 31/555* (2006.01)
*A61P 31/14* (2006.01)

(52) U.S. Cl.
CPC ............ *A61K 31/555* (2013.01); *A61P 31/14* (2018.01)

(58) Field of Classification Search
CPC .............................. A61K 31/555; A61P 31/14
See application file for complete search history.

(56) References Cited

U.S. PATENT DOCUMENTS 10,975,102 B1 4/2021 Al-Zaydi
11,104,692 B1 * 8/2021 Al-Zaydi .................. C07F 1/08
11,192,902 B1 * 12/2021 Al-Zaydi ................ C07F 1/005
2020/0390187 A1 12/2020 Pikul et al.
2022/0280529 A1 * 9/2022 Dumoulin-White ......................... A61K 31/555

OTHER PUBLICATIONS

West; Polyhedron 1999, 18, 2919. https://doi.org/10.1016/S0277-5387(99)00210-7 (Year: 1999).*
Tarasconi; Bioorg Med Chem. 2000, 8, 157. https://doi.org/10.1016/S0968-0896(99)00260-6 (Year: 2000).*
Beckford; Dalton Trans. 2009, 48, 10757. https://doi.org/10.1039/B915081A (Year: 2009).*
Pelosi; J. Med. Chem. 2010, 53, 24, 8765-8769. https://doi.org/10.1021/jm1007616 (Year: 2010).*
Feng; Coloration Technology 2017, 133, 312-319. https://doi.org/10.1111/cote.12282 (Year: 2017).*
Manjunath; Journal of Molecular Structure 2017, 1127, 314-321. http://dx.doi.org/10.1016/j.molstruc.2016.07.123 (Year: 2017).*
Li; Nat Rev Drug Discov 2020, 19, 149-150. https://doi.org/10.1038/d41573-020-00016-0 (Year: 2020).*
Ogando; Journal of General Virology 2020, 101, 925-940. https://doi.org/10.1099/jgv.0.001453 (Year: 2020).*
Howsaui; Appl. Sci. 2021, 11, 9067; https://doi.org/10.3390/app11199067 (Year: 2021).*
Al-Sulami; Inorganic Chemistry Communications 142 (2022) 109535. https://doi.org/10.1016/j.inoche.2022.109535 (Year: 2022).*
Basha; Appl Organomet Chem. 2023, 37, e6972. https://doi.org/10.1002/aoc.6972 (Year: 2023).*
Copper(II) Inhibition of the SARS-CoV-2 Main Protease, Garza-Lopez; ChemRxiv. Jul. 21, 2020. doi: 10.26434/chemrxiv.12673436. Preprint.

* cited by examiner

*Primary Examiner* — Daniel R Carcanague
(74) *Attorney, Agent, or Firm* — WCF IP

(57) ABSTRACT

Methods of using copper (II) complexes of Formula I to prevent and/or treat coronavirus infections, such as SARS-CoV-2 infections, are provided. In Formula I, Y is $NO_2$ or $CH_3$ and X is a C1 to C20 hydrocarbon which is optionally substituted. The copper (II) complexes bind to an inactivate proteins that are necessary for the virus to successfully establish an infection and reproduce.

Formula I

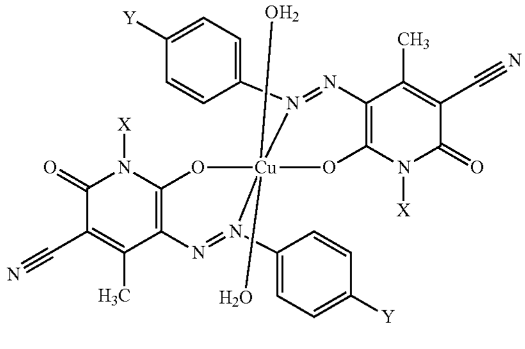

10 Claims, 22 Drawing Sheets

D1

D2

A1

A2

THERAPEUTIC INHIBITION AFFINITY OF COPPER (II) COMPLEX AND THEIR DIAZENYL PYRIDINONE HETEROCYCLIC LIGANDS AGAINST SARS-COV2

BACKGROUND OF THE INVENTION

Field of the Invention

The invention generally relates to improved therapeutic agents for preventing or treating coronavirus infection. In particular, the invention provides diazenyl pyridinone heterocyclic ligand-containing Cu(II) complexes as effective therapeutic agents against coronavirus infection, such as infection by SARS-CoV-2.

Description of Related Art

Coronavirus, SARS-CoV-2, is a novel beta-coronavirus with glycoprotein spikes arranged like a crown. The International Virus Classification Commission (ICTV) classified the novel beta-coronavirus that was first found in Wuhan, China, as Severe Acute Respiratory Syndrome Coronavirus 2 (SARS-CoV-2). Common symptoms of an infected person range from the flu-like symptoms to death. SARS-COV-2 not only infects the lower respiratory system inducing severe pneumonia, but also affects parts of the digestive system, heart, liver, kidneys, and nervous system, causing multi-organ failure and even death. Other coronaviruses also cause severe disease and death.

Artificial intelligence and molecular docking methods to screen target-virtual ligands provide tools to identify potential drug candidates against SARS-CoV-2. These tools have been directed to elucidating quantitative relationship between chemical structure and biological activity, allowing the prediction of theoretical bioactivity without an excessive amount of experimental time and effort.

Transition-metal ion complexes having highly dense heterocyclic ligands have numerous biological and pharmacological activities, including antifungal, antiviral, antibacterial, and antimalarial activities. Diazenyl derivatives have gained interest due to their potential therapeutic effects as antiviral, antidiabetic, antineoplastic, antiseptic, antifungal, and antimicrobial agents. 1,2,4-triazole and triazine heterocyclic moieties have proven antibacterial, antifungal, and anticancer activity. 1,2,3-triazole derivatives are established as novel inhibitors against coronavirus. Copper(II) complexes are of interest due to their essential role as cellular elements for many biological pathways, including cofactors in an enzyme catalytic process.

U.S. Pat. Nos. 10,975,102 and 11,104,692 to Al-Zaydi describes heterocyclic diazenyl pyridinone copper (II) complexes as pharmacological agents. The exact chemical structures of the complexes are disclosed here (including general structural formula I, where X=a C1 to C20 hydrocarbon, which is optionally substituted and where X may be the same or different at both locations). The complexes may be present in a pharmaceutical composition with a pharmaceutical carrier (e.g., fluid, solid, etc.) deliverable to a human or other animal by a variety of routes for the treatment (page 2, lines 10-50). In the Example, Al-Zaydi cites scientific research articles (e.g., Manjunath, M. et al., J. Mol. Struct., 2017, 1127, 314 and Badea, M. et al., J. Therm. Anal. calorim., 2014, 118, 1145) to provide background information on the copper complexes of thiosemicarbazones, which "have been studied for biological applications including antitumor, antifungal, antiviral, antibacterial, antifilarial, and antimalarial activities". However, no information regarding the use of the copper complexes for the treatment of SARS-CoV-2 is provided.

U.S. Patent Application 2020/0390187 to Pikul describes that the SARS-CoV-1 virus and the SARS-CoV-2 virus do not survive as long on copper as on other surfaces and indicates that SARS-CoV-2 is more sensitive to copper than SARS-CoV-1 (page 4, paragraph 33). Pikul states that an antiviral material can contain copper, copper chelate, a coordinated copper complex, or a copper-containing chemical structure (Cu(II) based mesityl, phenyl, or cyclohexyl group, or a Cu(II) complex that employs pyrrole-based chelates to stabilize the metal ion).

Garza-Lopez et al., (ChemRxiv, Preprint, 2020) describes an analysis of the structural stability of the coronavirus main protease (Mpro) and copper(II) chelates, which may dock in the Mpro enzyme active-site region, thus inhibiting SARS-CoV-2 infection by disrupting the enzymatic activity of the main protease of SARS-CoV-2.

SUMMARY OF THE INVENTION

The invention relates to a method of using copper (II) complexes to inhibit (e.g. prevent and/or treat) coronavirus infection, such as SARS-CoV-2 infection. The copper (II) complexes bind to an inactivate proteins that are necessary for the virus to successfully establish an infection and reproduce. The proteins include surface receptors of host cells that are used by the virus to enter the cell, and viral and host proteins that are required for viral replication and maturation. Exemplary targeted proteins include, for example, ACE2 (angiotensin-converting enzyme 2), TMPRSS2 (transmembrane protease serin 2), RDRP (RNA-dependent RNA polymerase), 3CLpro (3C-like protease), and PLpro (Papain-like protease). The disclosure also describes molecular docking methods for screening potential therapeutics based on measuring their target binding affinity.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a method of preventing or treating a SARS-CoV-2 infection in a subject in need thereof, comprising administering to the subject a therapeutically effective compound of Formula I:

Formula I

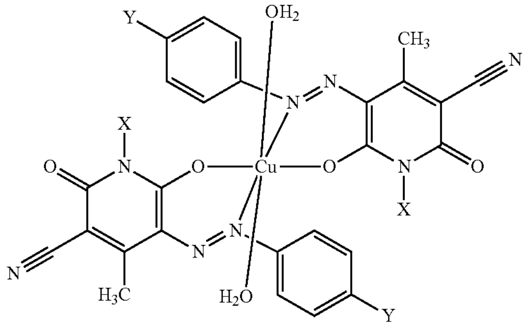

where Y is $NO_2$ or $CH_3$ and X=a C1 to C20 hydrocarbon which is optionally substituted. In some aspects, the compound is

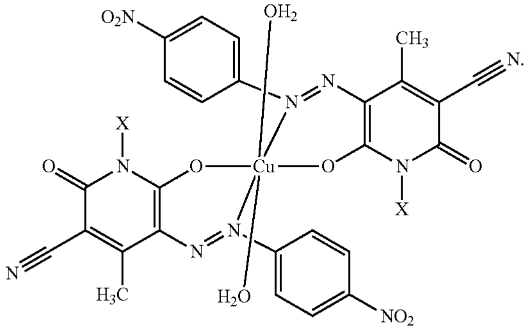

In other aspects, the compound is

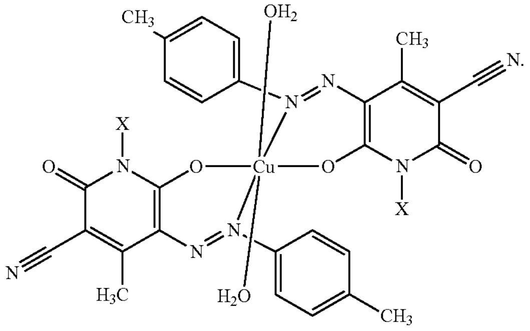

In further aspects, X=butyl, hexyl or benzyl.

In additional aspects, the compound is

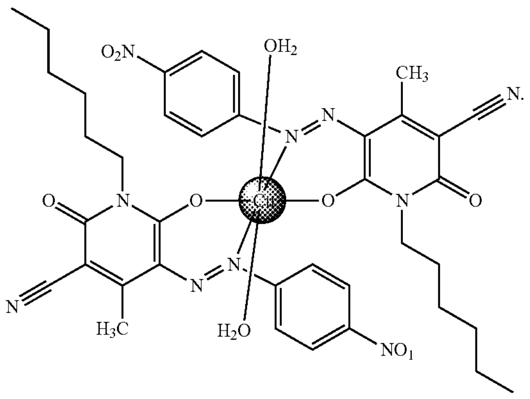

In yet further aspects, the compound is

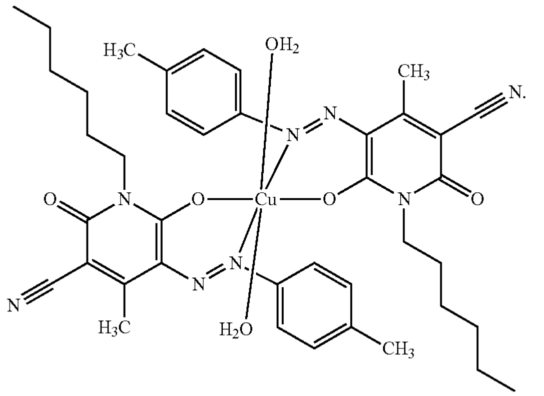

The invention also provides methods of preventing a SARS-CoV-2 virus from infecting a host cell, comprising contacting i) one or more viral proteins of the SARS-CoV-2 virus and/or ii) one or more surface receptor proteins of the host cell, with a compound of Formula I:

Formula I

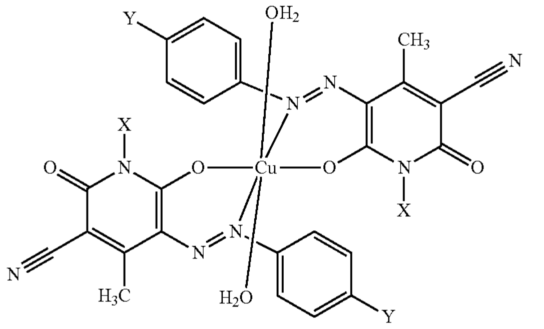

where Y is $NO_2$ or $CH_3$ and X=a C1 to C20 hydrocarbon which is optionally substituted. In some aspects, the compound is

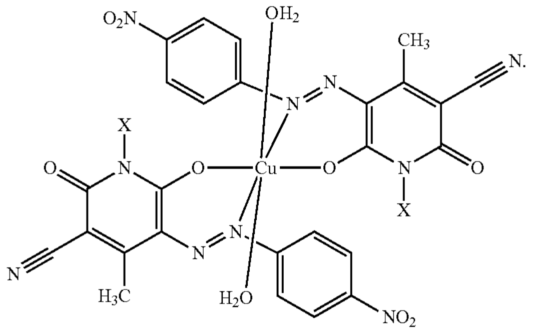

In other aspects, the compound is

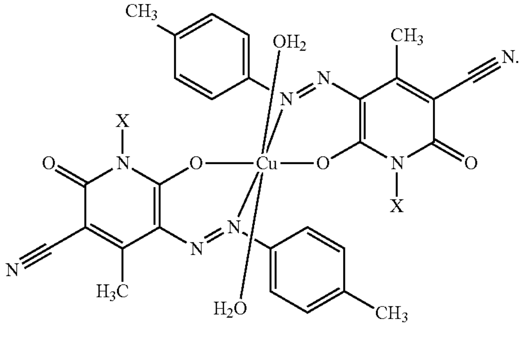

In further aspects, X=butyl, hexyl or benzyl.

In additional aspects, the compound is

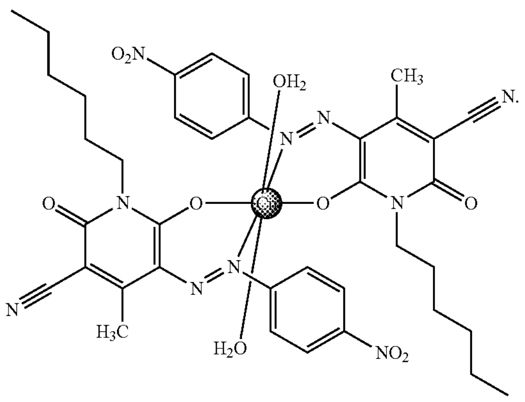

In yet further aspects, the compound is

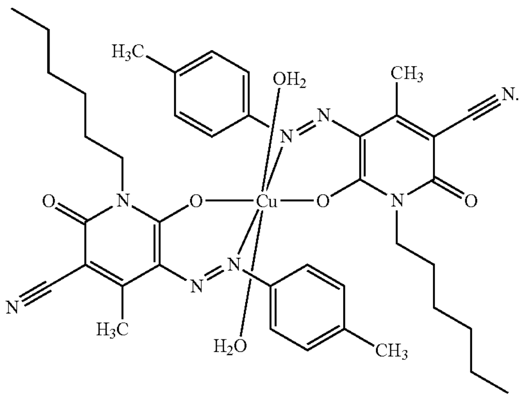

DETAILED DESCRIPTION

Figure 1:
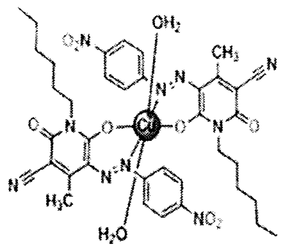
FIG. 1. Structure of Cu(II) complexes (D1, D2) and their diazenyl pyridinone ligands (A1, A2).
Figure 1:
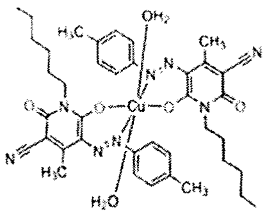
Figure 1:
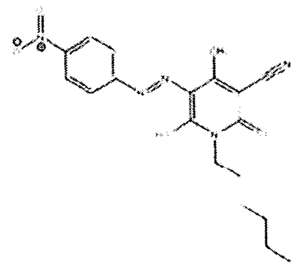
Figure 1:
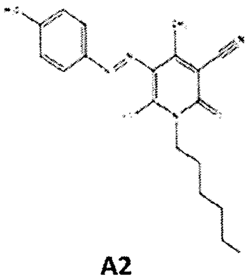

Provided herein are method of inhibiting the infection process of a coronavirus. In some aspects, the coronavirus is SARS-CoV-2. Compounds disclosed in issued U.S. Pat. Nos. 10,975,102 and 11,104,692, the complete contents of each of which is hereby incorporated by reference in entirety, have been assessed in order to determine their therapeutic inhibition affinity for SARS-CoV-2. The results are supported by in silico docking studies and indicate that the compounds are good inhibitors of the infectivity of the virus. Without being bound by theory, it is believed that the compounds function by targeting and blocking specific receptors on the host surface, including ACE2, TMPRSS 2, RdRP, 3CLpro, and PLpro, thereby preventing the coronavirus from entering host cells.

Accordingly, the present disclosure provides methods of using compounds of Formula I:

Formula I

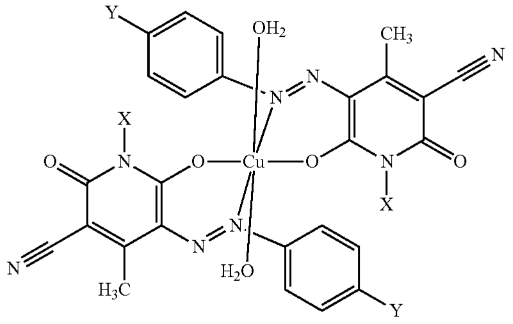

to prevent or treat coronavirus infections, such as coronavirus infections caused by SARS-CoV-2. Without being bound by theory, it is believed that administering one or more compounds of Formula Ito a subject results in the compound(s) interacting (such as binding to) one or more proteins that are necessary for viral entry into a host cell and/or subsequent viral replication and maturation. Binding of the compounds inactivates the proteins and thus blocks the pathway of infection, and/or blocks viral protein receptors, thereby preventing viral entry into and infection of the host cell.

In Formula I, X is C1 to C20 hydrocarbon which is optionally substituted, and Y is $NO_2$ (nitro) or $CH_3$ (methyl).

In the examples below the same substituent X was used at both locations; however, in the practice of the invention, X will be a C1 to C20 hydrocarbon which is optionally substituted and may be the same or different at the two locations. The C1 to C20 hydrocarbons include both aliphatic and aromatic hydrocarbons and may be substituted or unsubstituted.

Aliphatic hydrocarbons may be saturated or unsaturated, cyclic, linear or branched. Examples of aliphatic hydrocarbons include but are not limited to: methyl, ethyl, propyl, isopropyl, n-butyl, s-butyl, t-butyl, 2-butenyl, 2-butynyl, pentyl, hexyl, heptyl, octyl, nonyl, etc.

Cyclic aliphatic hydrocarbons (cycloalkyls) are a subset of hydrocarbons and includes cyclic hydrocarbon groups of from e.g. about 3 to 8 carbon atoms. Examples of cycloalkyl groups include but are not limited to: cyclopropyl, cyclobutyl, cyclopentyl, norbornyl, and the like.

Aromatic (aryl) hydrocarbons include but are not limited to: the simple aryl group phenyl (with the chemical formula $C_6H_5$), a group derived from benzene; the tolyl group, $CH_3C_6H_4$, which is derived from toluene (methylbenzene); the xylyl group, $(CH_3)_2C_6H_3$, which is derived from xylene (dimethylbenzene); the naphthyl group, $C_{10}H_8$, which is derived from naphthalene; etc.

The C1 to C20 hydrocarbon groups which include aliphatic and aromatic groups are optionally substituted. As used herein, the term "optionally substituted" may be used interchangeably with "unsubstituted or substituted". The term "substituted" refers to the addition of one or more substituents by replacement of a carbon atom or as an attachment to a carbon atom. In some embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy. Additional examples include: substituted alkyl, aryl, cycloalkyl, etc. wherein one or more H atoms are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl, alkoxycarbonylamino, aminocarbonyl (also known as carboxamido), alkylaminocarbonyl, cyano, acetoxy, nitro, amino, alkylamino, dialkylamino, (alkyl)(aryl) amino alkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical.

Cyclic and aromatic hydrocarbons may also be heterocyclic. Heterocyclic means an aliphatic or aromatic carbocycle in which from one to four carbons is replaced by a heteroatom, examples of which include but are not limited to N, O, or S. Heterocycles may also be optionally substituted, e.g by the attachment of a substituent to the ring as described above. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include but are not limited to: pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

In some aspects, the C1 to C20 hydrocarbon is butyl, hexyl or benzyl.

In further aspects, the compounds are:

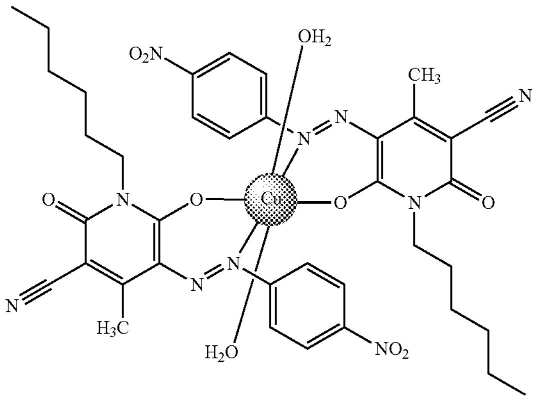

D1: 4,4-bis[(dimethylamino)methoxy]-7,7'-dihexyl-10,10'-dimethyl-3,3'-bis(4-nitrophenyl)-8,8'-dioxo-4,4'-spirobi[5-oxa-2,7-diaza-3-azonia-4λ$^6$-cuprabicyclo[4.4.0]deca-1(6),2,9-triene]-9,9'-dicarbonitrile or

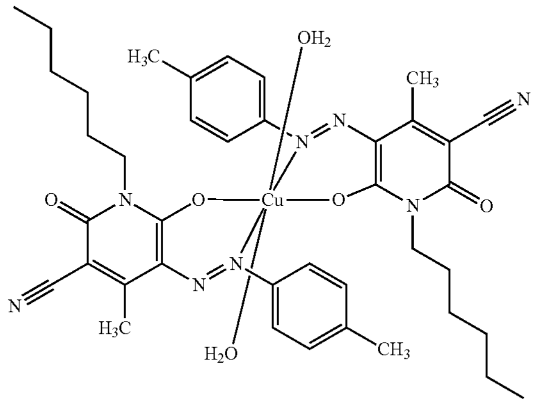

D2: 7,7'-dihexyl-10,10'-dimethyl-8,8'-dioxo-3,3'-bis(p-tolyl)-4,4'-spirobi[5-oxa-2,7-diaza-3-azoni a-4λ$^4$-cuprabicyclo[4.4.0]deca-1(6),2,9-triene]-9,9'-dicarbonitrile.

Pharmaceutical Preparations

The compounds (complexes) described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders, various dosage forms, and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as Tween™ 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Administration

The terms "administer", "administering" or "administration" in reference to a dosage form of the invention refers to the act of introducing the dosage form into the system of a subject in need of treatment.

Treatment involves administering a therapeutically effective amount of a compound described herein to a patient diagnosed with a disease (e.g. a coronavirus infection) and may involve administering the compound to a patient who does or does not have active symptoms. Conversely, treatment may involve administering the compositions to a patient at risk of developing a particular disease (e.g. a coronavirus infection), or to a patient reporting one or more of the physiological symptoms of a disease (e.g. a coronavirus infection), even though a diagnosis of this disease may not have been made.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved when one or more of the physiological symptoms associated with the disease is ameliorated such that an improvement is observed in the patient, notwithstanding that the patient may still be afflicted with the disease. A "therapeutically effective" amount may also refer to an amount that prevents the disease. Those of skill in the art will recognize that although the complete eradication of symptoms is a preferred outcome, much advantage accrues if symptoms are only lessened or delayed, the duration of the illness is shortened, hospitalization is prevented, intubation is prevented, death is prevented, etc.

The compositions comprising the complexes may be administered in vivo by any suitable route including but not limited to: inoculation or injection (e.g. intravenous, intraperitoneal, intramuscular, subcutaneous, intra-aural, intraarticular, intramammary, and the like), and by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), intravaginally, intranasally, rectally, as eye drops, etc. In preferred embodiments, the mode of administration is by injection, e.g. intravenous or by inhalation into the lungs. Administration also includes e.g. via a mask worn over the mouth and nose, the mask having been permeated or coated with one or more of the compounds. Medical equipment and/or medical gowns, gloves, caps, etc. may be permeated or coated with the compounds. Similarly, the compounds may be included e.g. in disinfectant and cleaning solutions, hand sanitizers, and the like.

In addition, the compositions may be administered in conjunction with other treatment modalities such as substances that boost the immune system, various chemotherapeutic agents, pain medication, medications to reduce fever, vaccines, antibody therapy, anti-viral agents, etc. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

The subjects that are treated can be any that have or are suspected of or are at risk to be infected by a coronavirus, especially SARS-CoV2. The subject may be of any gender or age. Generally, the subject is a mammal, typically a human, although veterinary applications of this technology are also encompassed, e.g for animals that are susceptible to coronavirus infections.

The dose of a complex that is administered may be any that is suitable for the particular patient. Generally, the dose ranges from about 1 to about 500 mg/kg of body weight, such as about 1, 10, 20, 30, 40, 50, 60, 70, 80, 90, 100, 150, 200, 250, 300, 350, 400, 450 or 500 mg/kg, or even more, including all single digit integers between these values.

In preferred aspects, the coronavirus is a SARS-CoV or SARS-CoV-2 virus or a variant thereof. Variants of SARS-CoV-2 include but are not limited to alpha, beta, gamma, delta, omicron, and any others of interest.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms “a”, “an”, and “the” include plural referents unless the context clearly dictates otherwise. It is further noted that the claims may be drafted to exclude any optional element. As such, this statement is intended to serve as support for the recitation in the claims of such exclusive terminology as “solely,” “only” and the like in connection with the recitation of claim elements, or use of a “negative” limitations, such as “wherein [a particular feature or element] is absent”, or “except for [a particular feature or element]”, or “wherein [a particular feature or element] is not present (included, etc.) . . . ”.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1. Preparation of the Complexes

The copper(II)-complexes (D1, D2) were synthesized by the following general method: (2 mmol) of each ligand (A1, 0.445 g) and (A2, 0.376 g) was dissolved in 20 ml of hot ethanol. (see Scheme I). Then, a solution of the $CuCl_2$ salt (0.171 g, 1 mmol) was added dropwise with constant stirring, followed by adding few drops of an aqueous solution of sodium hydroxide NaOH (0.5 M) to adjust the PH at 8. The mixture was gently refluxed for 2 h at 50° C. Under reduced pressure, the volume was condensed to half of the initial amount. Then, the solid precipitation of Cu(II) complexes that separated out upon slow cooling at room temperature, filtered off, washed with cold ethanol (10 mL), followed by diethyl ether (10 mL), and dried in vacuum over anhydrous $CaCl_2$. The crude products of Cu(II) complexes (D1, D2) were recrystallized from DMF and DMSO solvents, respectively at room temperature.

Example 2. In Silico Analysis

Based on the fact that copper complexes are water-insoluble, molecular modeling analyses of spike protein (S) on cell surface molecules of a viral host play a major role in the determination of tissue and host species tropism of viruses.

This Example describes the results of in silico docking experiments which identified diazenyl pyridinone heterocyclic ligands suitable for use as models to mimic (serve as “stand-ins”) for the viral ligand protein that binds to a host receptor protein, e.g. during viral infection of a host cell. Once identified, the ligands were used to estimate the therapeutic inhibition affinity of several copper(II) complexes for the viral ligand since blocking the host protein(s) would prevent the virus from binding to and infecting the cell, and/or from undergoing replication and maturation. Further in vitro experiments showed that the copper(II) complexes do in fact, inhibit the infection process of SARS-CoV-2, as predicted using the in silico data.

Compound Structure Preparation for Docking Assessment

The preparation of the structure of the test compounds was done by converting CIF files into MOL files. The resulting three-dimensional structures of the compounds were used for the docking process.

Protein “Preparation”

Coronaviruses are viruses having glycoprotein spikes that are arranged on their outer surface like a crown. Coronaviruses infect a host cell in three identified stages. In the first stage, the virus attaches to a host cell via the transmembrane spike glycoprotein binding to the angiotensin-converting enzyme 2 (ACE 2) receptor. A complex is formed between the S-glycoprotein and ACE-2 with the help of the transmembrane protease, serine 2 (TMPRSS2), which is produced by host cells. The next stage is the replication stage, during which the virus uses virus-encoded RNA-dependent RNA polymerase (RdRp) to make new RNA copies. The last stage is the maturation stage which occurs within the host cell by employing virus-encoded proteases such as 3CLpro (3C-like protease) and PLpro (Papain-like protease).

The ability of compounds to inhibit the infection process of SARS-CoV-2 was investigated in silico using molecular docking. “Protein preparation” involves selecting a sterically accessible chain of a target protein (e.g. a host protein) that binds with an appropriate native ligand (e.g. a SARS-CoV-2 protein). The target proteins of interest were ACE2, TMPRSS 2, RdRP, 3CLpro, and PLpro. The coordinates for conducting the searches, namely ACE2 (PDB ID: 1O86), TMPRSS2 (PDB ID: 5CE1), RdRp (PDB ID: 6NUR), 3CLpro (PDB ID: 2GTB), and PLpro (PDB ID: PDB ID:4OW0), were downloaded from the website located at http://www.rcsb.org. The goal of protein preparation is, using an in silico model of a protein (such as a host protein) bound to a ligand (such as a viral protein), to separate the ligand from the target protein in order to identify a pattern of sterically accessible atoms and functional groups located at the binding site of the target protein. This information is used to design a theoretical molecule (chain) comprising atoms and functional groups which are positioned or located so as to mimic the positions of the atoms and functional groups in the authentic protein. The use of a sterically accessible chain simplifies and enables easier determination of how a protein coordinates with atoms in the binding pocket of a ligand during docking analysis. Using the host ACE protein, Ligands A1 and A2 were identified (see FIG. 1). The method can be applied to any coronavirus protein, e.g. ACE2, TMPRSS2, RdRP, 3CLpro, PLpro, etc.

Ligand A1=1-hexyl-6-hydroxy-4-methyl-5-(4-nitrophenyl)azo-2-oxo-pyridine-3-carbonitrile

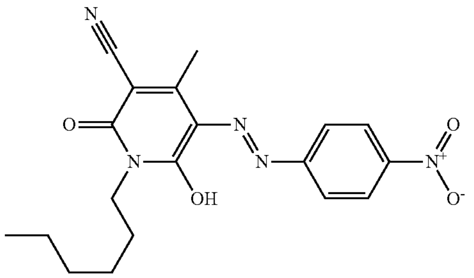 [SMILES: CCCCCCn1c(O)c(/N=N/c2ccc([N+](=O)[O-])cc2)c(C)c(C#N)c1=O]

Complex D1=4,4-bis[(dimethylamino)methoxy]-7,7'-dihexyl-10,10'-dimethyl-3,3'-bis(4-nitrophenyl)-8,8'-dioxo-4,4'-spirobi[5-oxa-2,7-diaza-3-azonia-4λ$^6$-cuprabicyclo[4.4.01]deca-1(6),2,9-triene]-9,9'-dicarbonitrile Ligand A2=1-hexyl-6-hydroxy-4-methyl-2-oxo-5-p-tolylazo)pyridine-3-carbonitrile

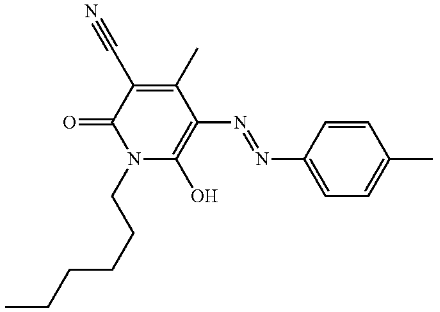 [SMILES: CCCCCCn1c(O)c(/N=N/c2ccc(C)cc2)c(C)c(C#N)c1=O]

Complex D2=7,7'-dihexyl-10,10'-dimethyl-8,8'-dioxo-3,3'-bis(p-tolyl)-4,4'-spirobi[5-oxa-2,7-diaza-3-azonia-4λ$^4$-cuprabicyclo[4.4.0]deca-1(6),2,9-triene]-9,9'-dicarbonitrile

Docking Method

All docking studies were performed by using the MOE program. The parameters and charges were assigned with the MMFF94x force field. Alpha-site spheres were generated using the site finder module of MOE. All calculations were carried out on an Intel® core (TM)i7, 3.8 GHz based machine running MS Windows 10 as the operating system. The Dock scoring in MOE software was done utilizing triangle matcher displacement methodology and rigid receptor and London dG for initial scoring methodology and GBVI/WSA dG function for final scoring. Auto rotatable bonds were allowed. The best 30 placements which passed the initial refinement were followed by 5 poses for output refinement to identify the final binding poses.

To compare the docking poses to the ligand in the co-crystallized structure and to obtain RMSD of the docking pose, a database browser was used. In order to rank the binding affinity of all compounds to the protein molecule, the binding free energy and hydrogen bonds between the compounds and the amino acids in the receptor were used. Evaluation of the hydrogen bonds was done by measuring the hydrogen bond length, which does not exceed 3.5 Å. Also, the RMSD of the compound position compared to the docking pose was used in ranking. Both RMSD as well as the mode of interaction of the native ligand within the structure of the receptor were used as a standard docked model.

Single-Crystal X-Ray Structure Determination of D1

TABLE 1

Crystallographic data and structure refinement details of D1 complex.

| Complex code | D1 |
|---|---|
| Formula | $C_{44}H_{54}CuN_{12}O_{10}$ |
| T/K | 120 |
| M/g · mol$^{-1}$ | 974.54 |
| Crystal system | Triclinic |
| Space group | P-1 (2) |
| a/Å | 8.7981 (3) |
| b/Å | 11.3934 (4) |
| c/Å | 11.8737 (4) |
| α/° | 88.133 (1) |
| β/° | 79.305 (1) |
| γ/° | 82.444 (1) |
| V/Å$^3$ | 1159.35 (7) |
| Z | 1 |
| $\rho_{calc}$/g · cm$^{-3}$ | 1.396 |
| μ/mm$^{-1}$ | 0.542 |
| Reflections | 114302 |
| $R_{int}$ | 0.0431 |
| Parameters | 308 |
| $R_1$ [I > 4σI][a] | 0.0364 |
| wR2[all data] | 0.1045 |
| S[c] | 1.071 |
| Max./min./e · Å$^3$ | 0.661/−0.787 |

[Cu(L)$_2$(dmf)$_2$] The Crystal Structure of Cu-Complex (D1) Using Ligand (A1)

Ligand A1=1-hexyl-6-hydroxy-4-methyl-5-(4-nitrophenyl)azo-2-oxo-pyridine-3-carbonitrile

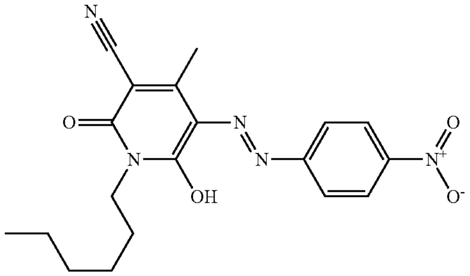 [SMILES: CCCCCCn1c(O)c(/N=N/c2ccc([N+](=O)[O-])cc2)c(C)c(C#N)c1=O]

Figure 2:
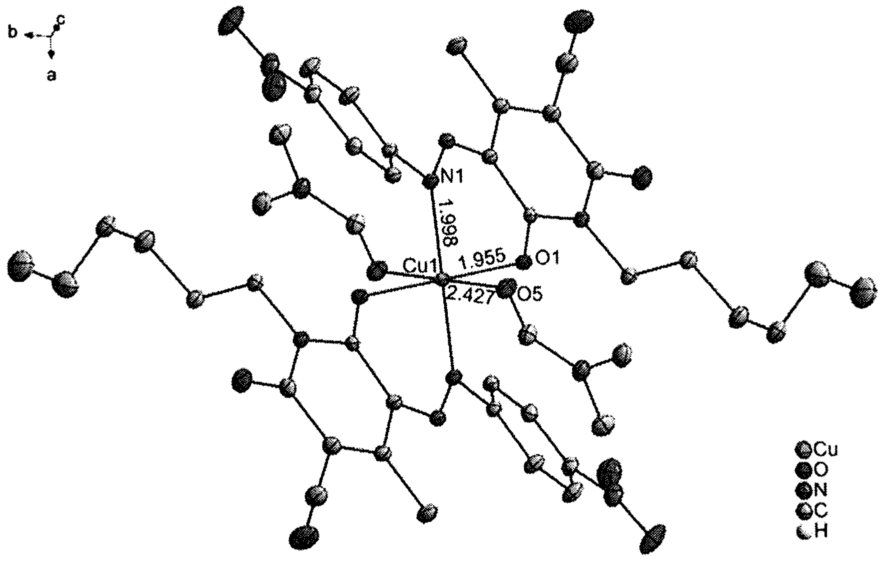
FIG. 2. Representation of the molecular structure of the D1 complex. The thermal ellipsoids are drawn with 50% probability.
Figure 3:
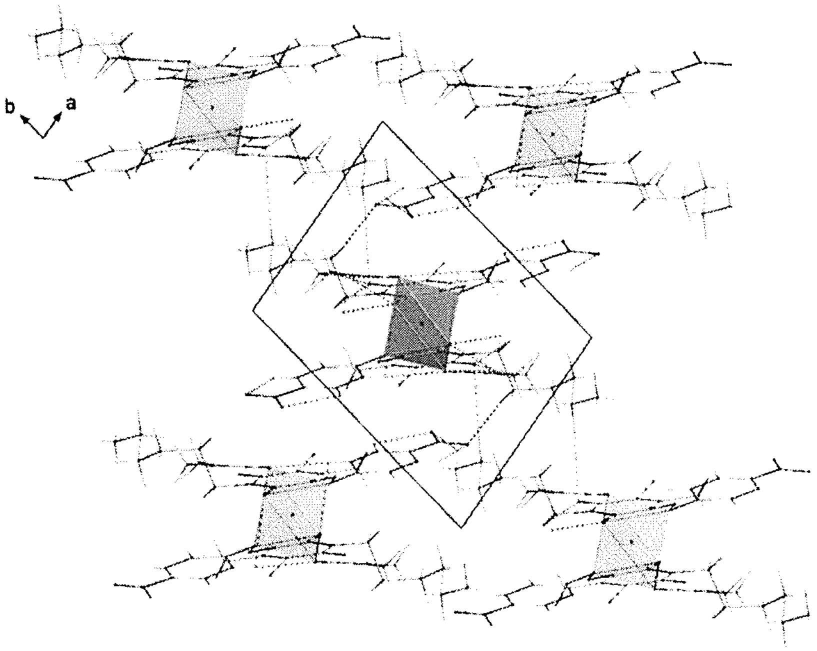
FIG. 3. Packing diagram of D2. D1 complex molecules packed along [110] via intermolecular H-bonding, depicted by dotted lines, to form 3D extended supramolecular network.

Complex D1=4,4-bis[(dimethylamino)methoxy]-7,7'-dihexyl-10,10'-dimethyl-3,3'-bis(4-nitrophenyl)-8,8'-dioxo-4,4'-spirobi[5-oxa-2,7-diaza-3-azonia-4λ$^6$-cuprabicyclo[4.4.0]deca-1(6),2,9-triene]-9,9'-dicarbonitrile The structure adopts triclinic lattice with P$\bar{1}$ (2) symmetry (Table 1). In this compound, the octahedral coordination environment of Cu is completed by two L ligands and two co-crystallized DMF molecules. The ligands are attached to the Cu-atom by the nitrogen atom of the diazenyl-group and the oxygen atom of the oxidaneyl group with d(Cu—N4)=1.998(1) Å and d(Cu—O1)=1.955(1) Å FIG. 2. The DMF solvent molecules coordinate the Cu atom through oxygen atoms with d(Cu—O5)=2.427(1) Å. The compound also has intra- and intermolecular hydrogen bonding with C—O . . . H distances ranging from 2.336(1) Å to 2.722(1) Å. The extended supramolecular framework is formed by packing of the molecules along [110] with the help of intermolecular H-bonding FIG. 3.

Structure Determination of D2

TABLE 2

Crystallographic data and structure refinement details of D2 complex.

| | |
|---|---|
| Complex code | D2 |
| Formula | $C_{40}H_{46}CuN_8O_4$ |
| T/K | 120 |
| M/g · $mol^{-1}$ | 766.4 |
| Crystal system | Monoclinic |
| Space group | $P2_1/c$ (14) |
| a/Å | 9.5534 (2) |
| b/Å | 12.9787 (3) |
| c/Å | 15.3298 (4) |
| α/° | 90 |
| β/° | 96.718 (1) |
| γ/° | 90 |
| V/$Å^3$ | 1887.70 (8) |
| Z | 2 |
| $\rho_{calc}$/g · $cm^{-3}$ | 1.348 |
| μ/$mm^{-1}$ | 1.239 |
| Reflections | 22695 |
| $R_{int}$ | 0.0459 |
| Parameters | 244 |
| $R_1$ [I > 4σI][a] | 0.0392 |
| wR2[all data] | 0.1138 |
| S[c] | 1.043 |
| Max./min./e · $Å^3$ | 0.690/−0.520 |

The crystal structure of Cu-complex (D2) using the ligand of (A2),

Ligand A2=1-hexyl-6-hydroxy-4-methyl-2-oxo-5-(p-tolylazo)pyridine-3-carbonitrile

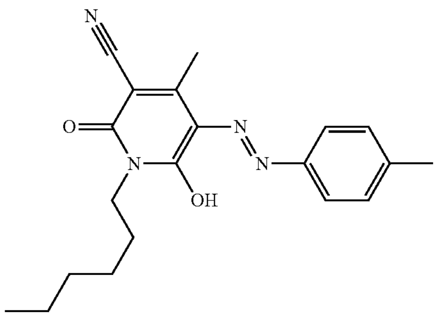 [SMILES: CCCCCCn1c(O)c(/N=N/c2ccc(C)cc2)c(C)c(C#N)c1=O]

Figure 4:
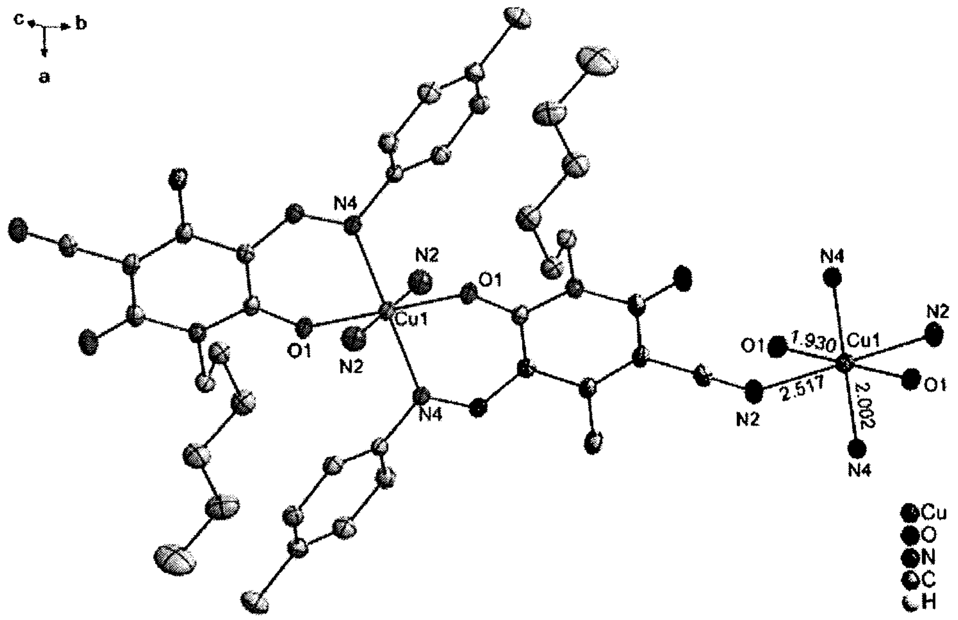
FIG. 4. Perspective view of the molecular structure along [111] reflecting the coordination of the ligands to the central Cu atom.
Figure 5:
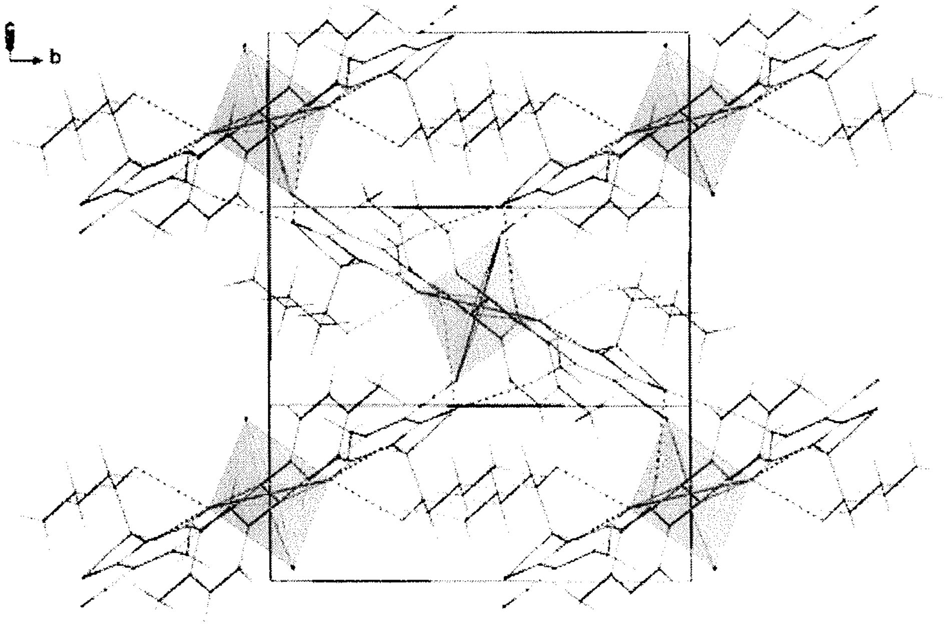
FIG. 5. Packing diagram of D2. Coordination of the central atoms are displayed with octahedra, and intra- and intermolecular H-bonding is depicted by dotted lines FIG. 6A-D. 3d Docking of the complex D1, D2 and ligand A1, A2 with S-Spike protein receptor 1O86 of SARS-CoV-2. A, Ligand A1; B, Complex D1; C, Ligand A2; D, Complex D2.
Figure 6A:
Figure 6B:
Figure 6C:
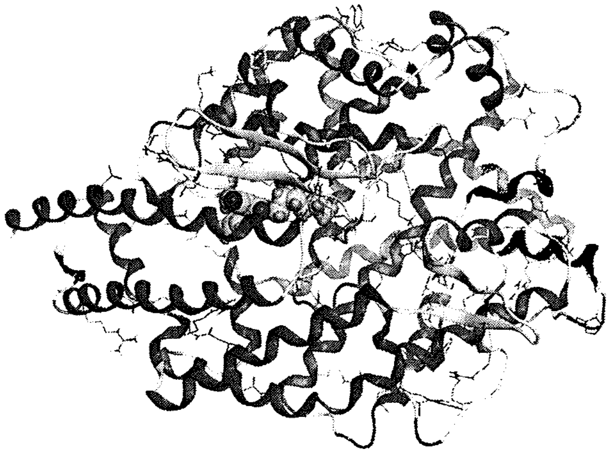
Figure 6D:
Figure 7A:
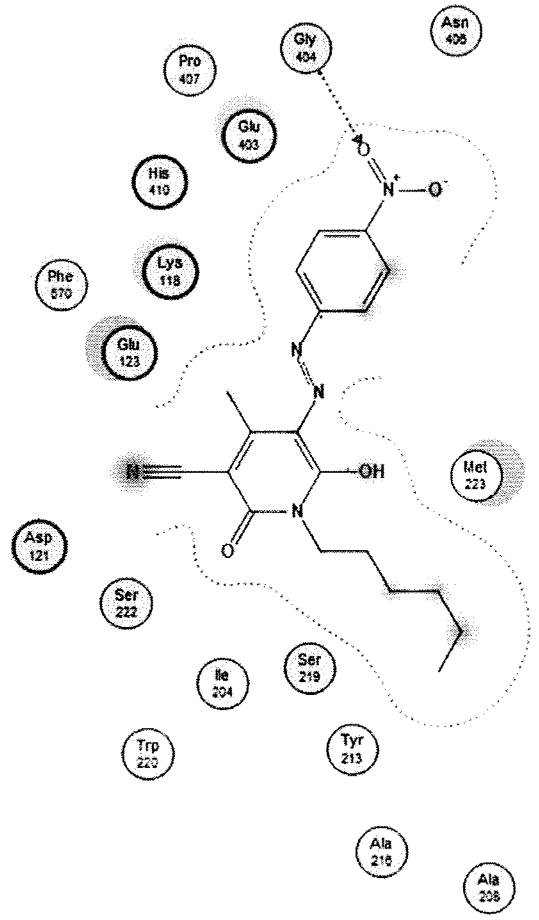
FIG. 7A-D. 2d Docking of the complex D1, D2 and ligand A1, A2 with S-Spike protein receptor 1O86 of SARS-CoV-2. A, Ligand A1; B, Complex D1; C, Ligand A2; D, Complex D2.
Figure 7B:
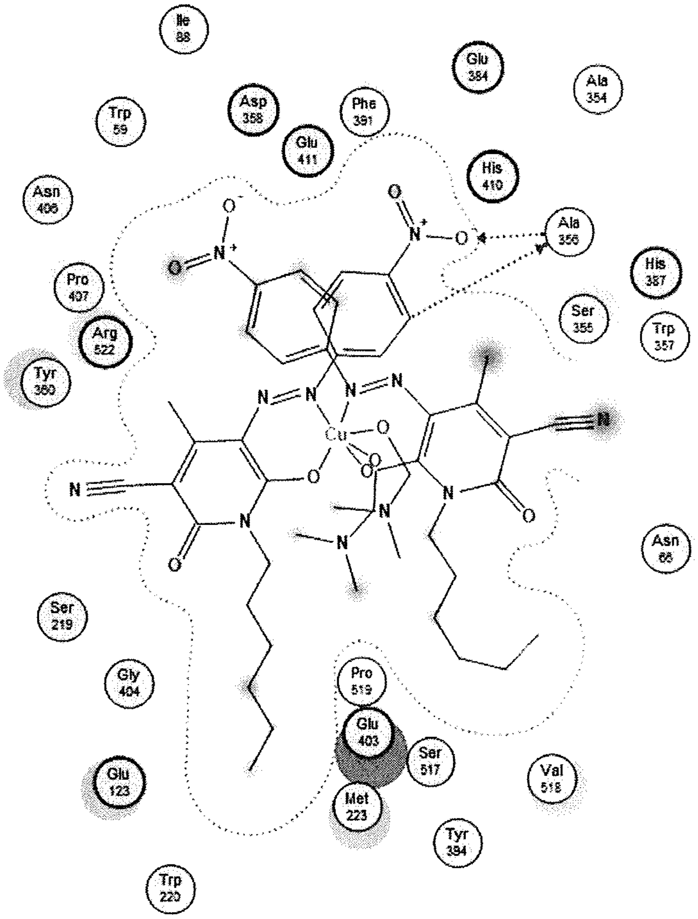
Figure 7C:
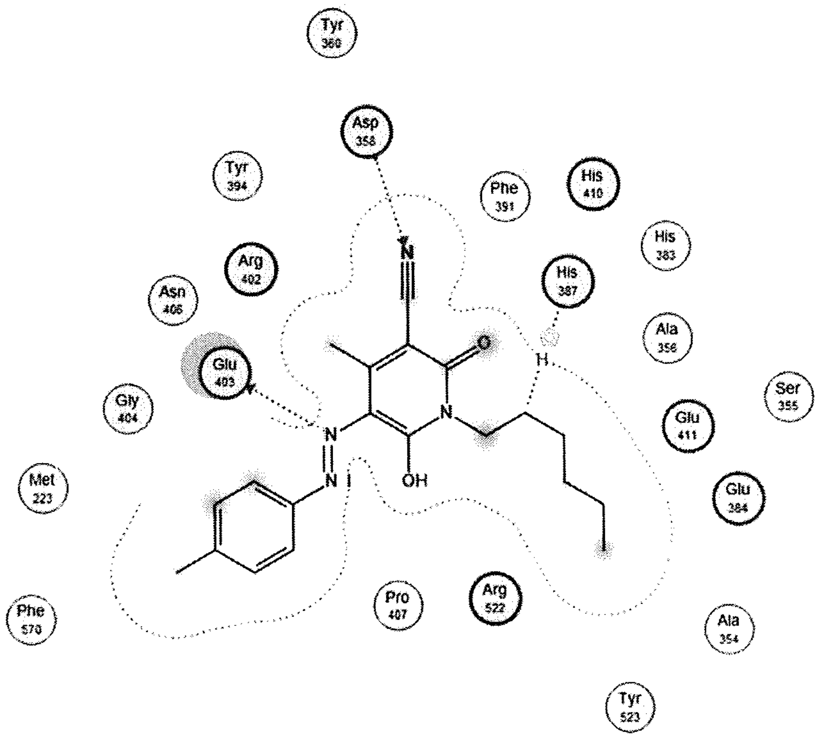
Figure 7D:
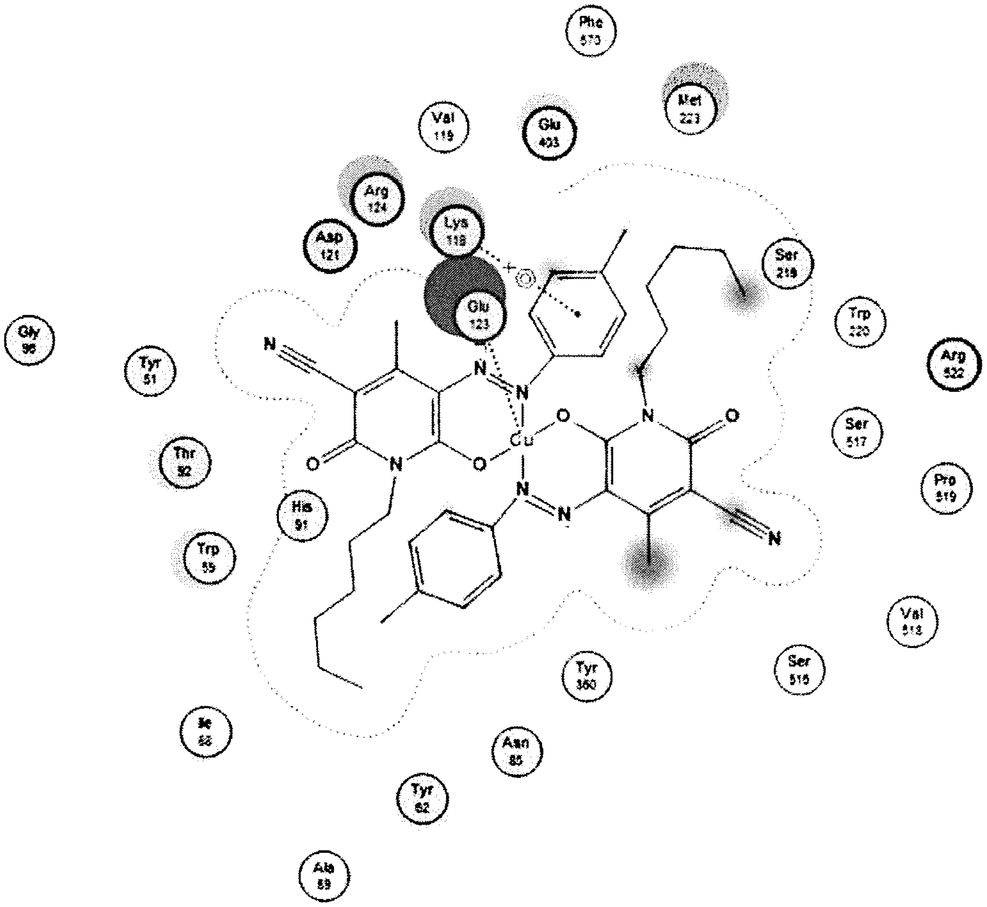
Figure 8A:
FIG. 8A-D. 3d Docking of the complex D1, D2 and ligand A1, A2 with receptor 5CE1 of SARS-CoV-2. A, Ligand A1; B, Complex D1; C, Ligand A2; D, Complex D2.
Figure 8B:
Figure 8C:
Figure 8D:
Figure 9A:
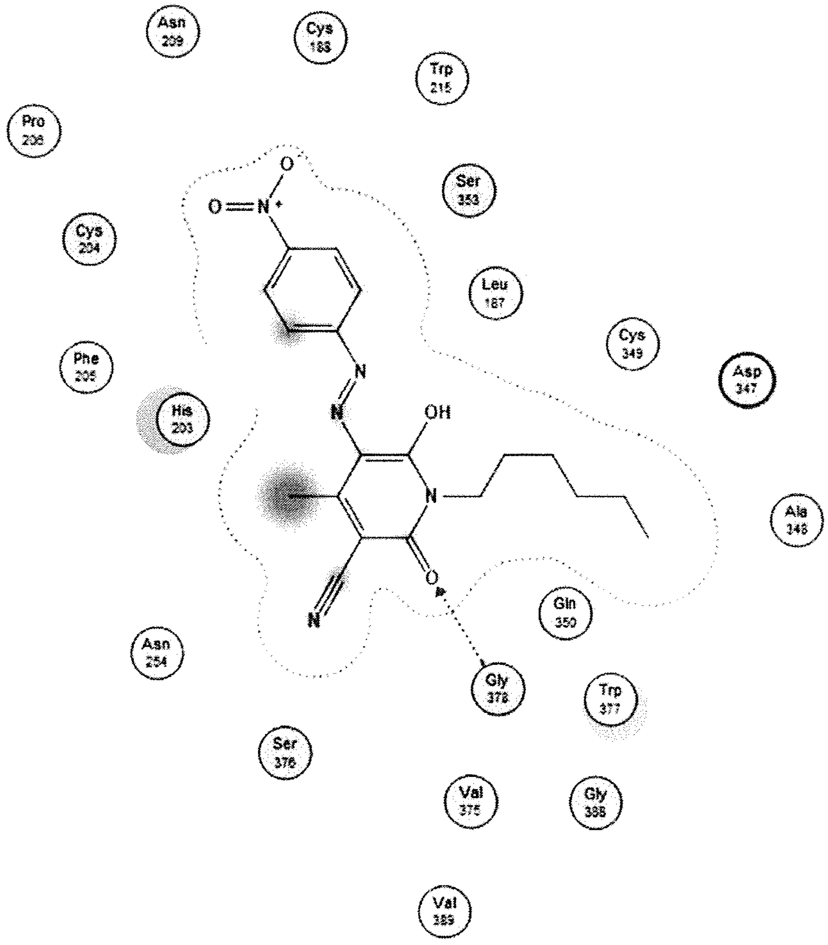
FIG. 9A-D. 2d Docking of the complex D1, D2 and ligand A1, A2 with protein receptor 5CE1 of SARS-CoV-2. A, Ligand A1; B, Complex D1; C, Ligand A2; D, Complex D2.
Figure 9B:
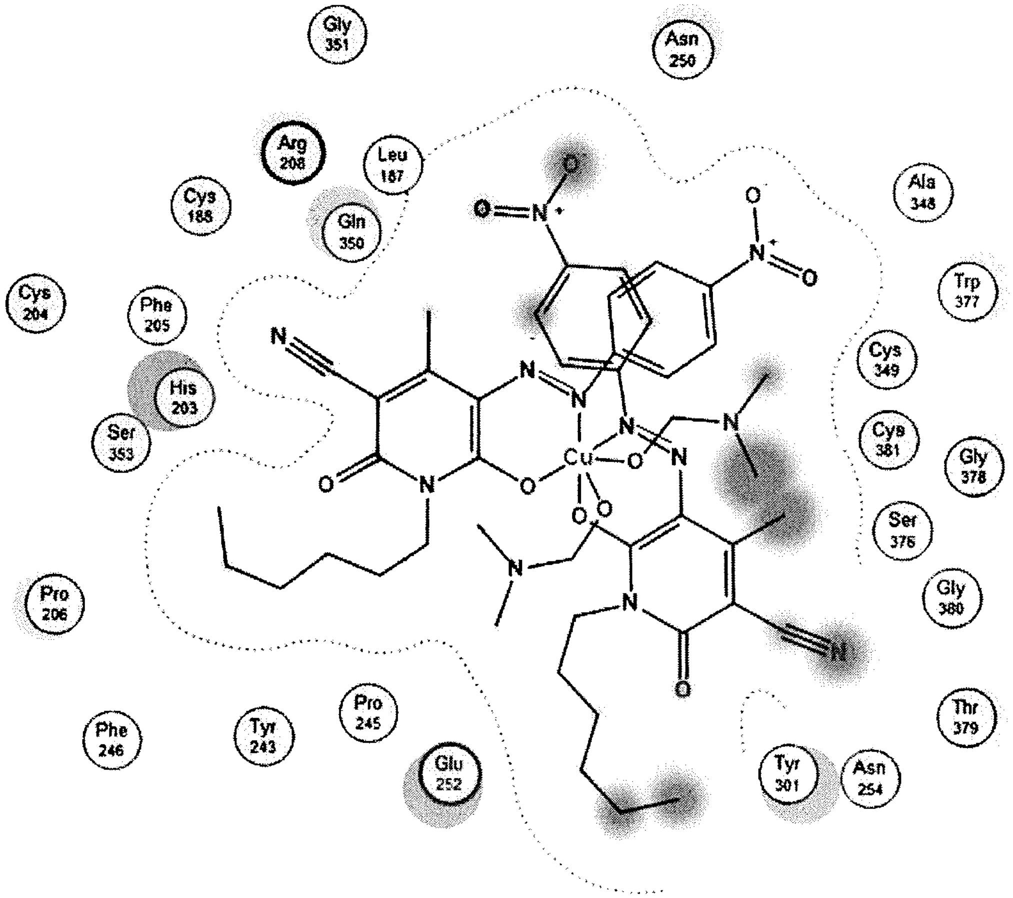
Figure 9C:
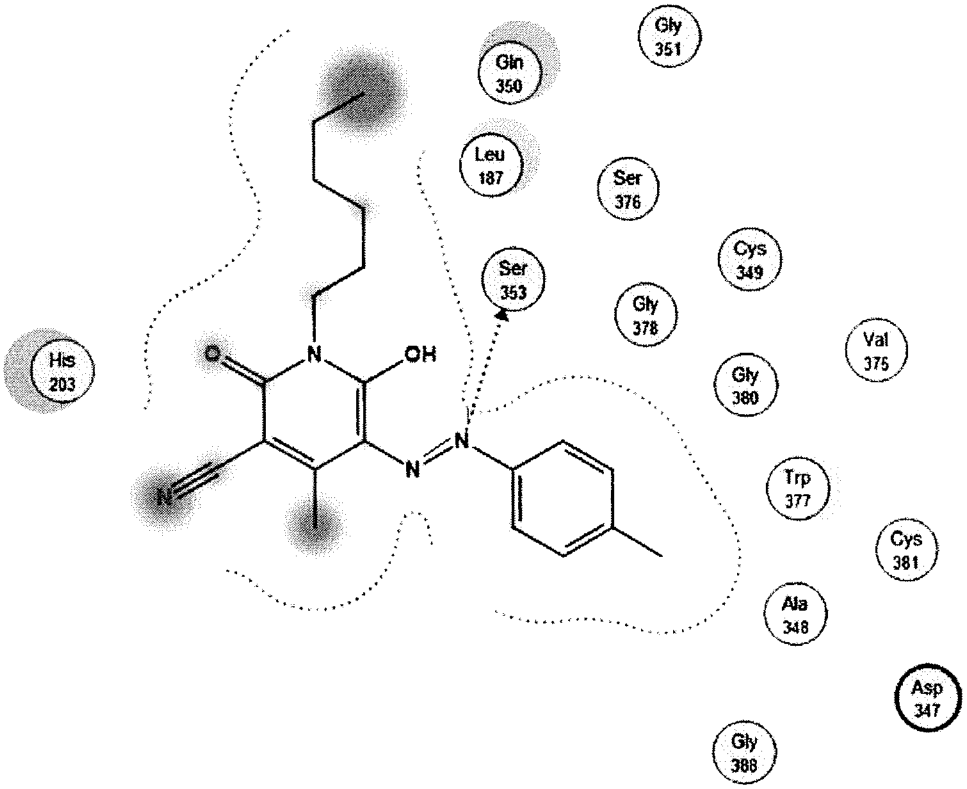
Figure 9D:
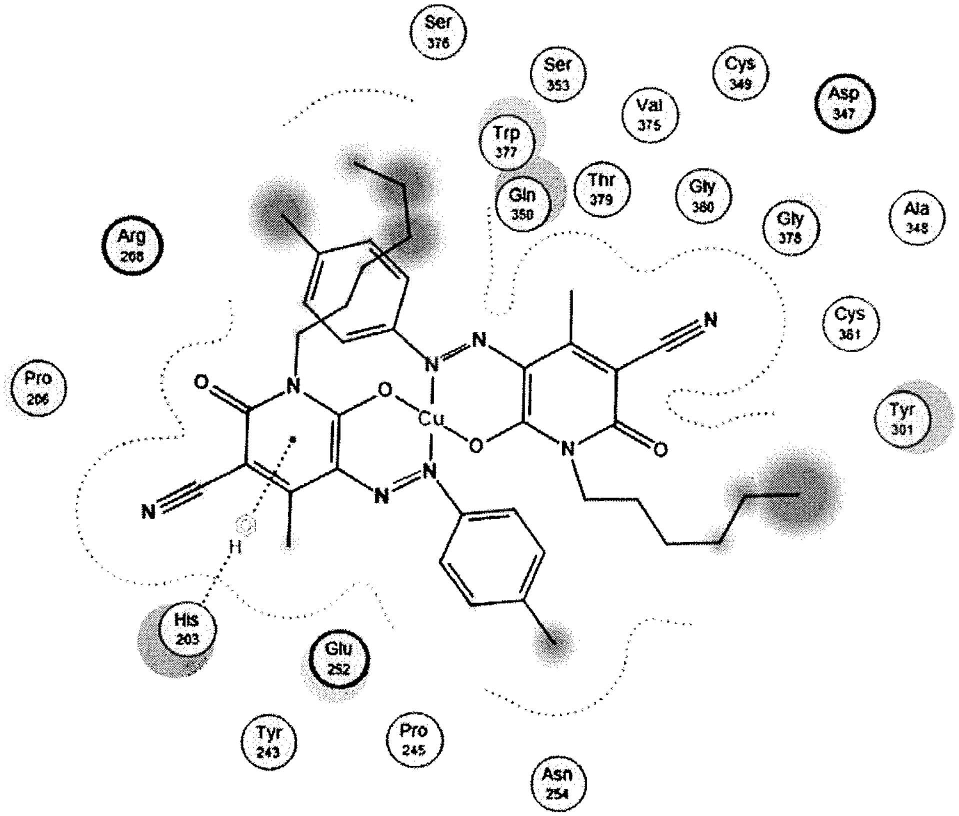
Figure 10A:
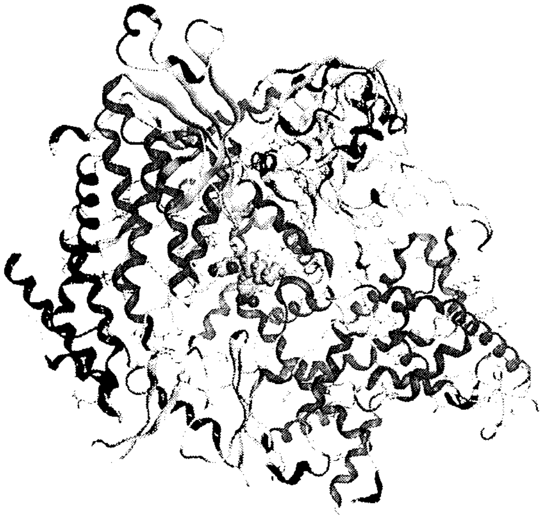
FIG. 10A-D. 3d Docking of the complex D1, D2 and ligand A1, A2 with receptor 6NUR of SARS-CoV-2. A, Ligand A1; B, Complex D1; C, Ligand A2; D, Complex D2.
Figure 10B:
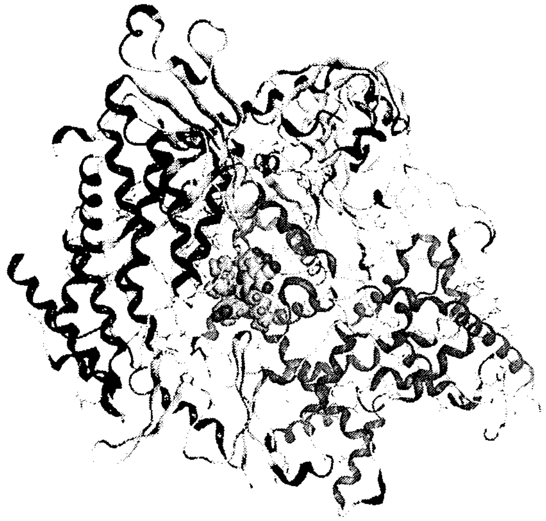
Figure 10C:
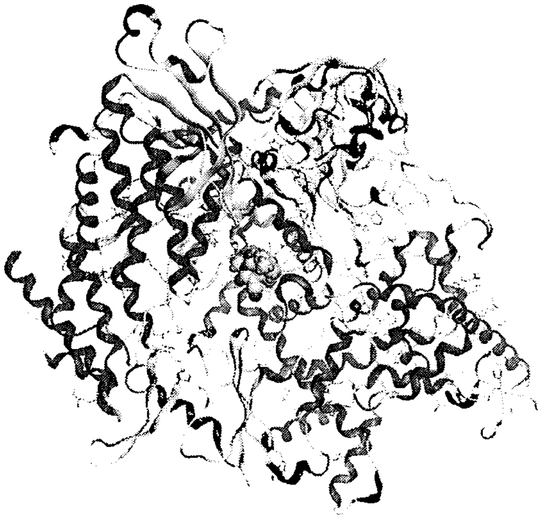
Figure 10D:
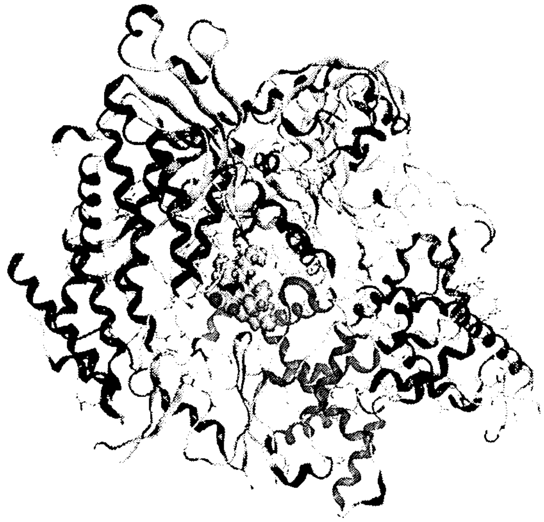
Figure 11A:
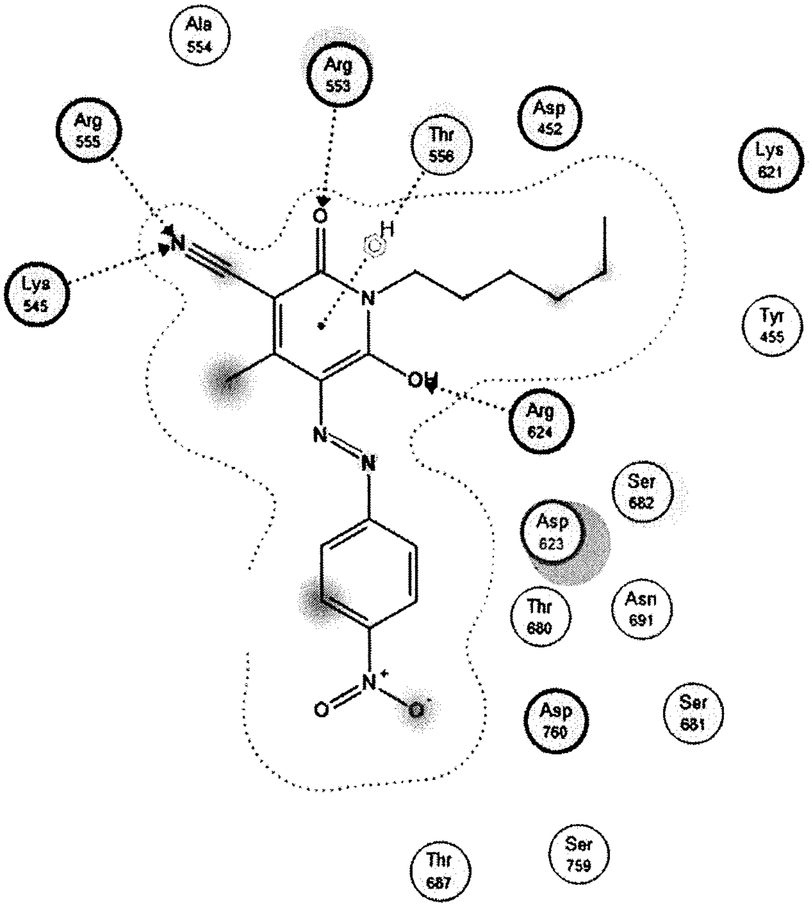
FIG. 11A-D. 2d Docking of the complex D1, D2 and ligand A1, A2 with protein receptor 6NUR of SARS-CoV-2. A, Ligand A1; B, Complex D1; C, Ligand A2; D, Complex D2.
Figure 11B:
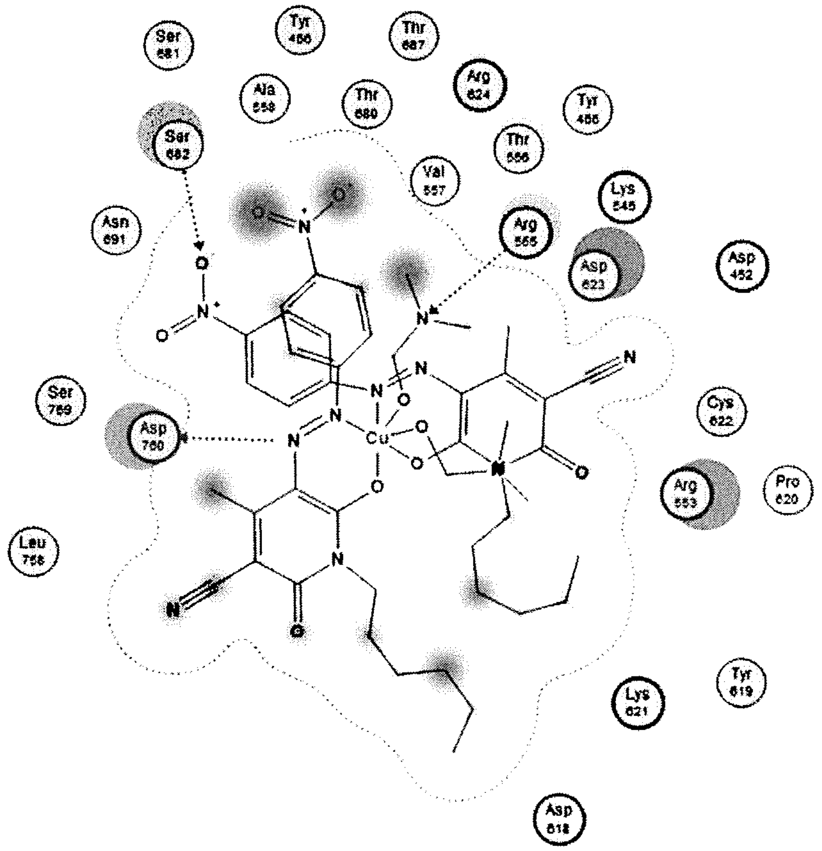
Figure 11C:
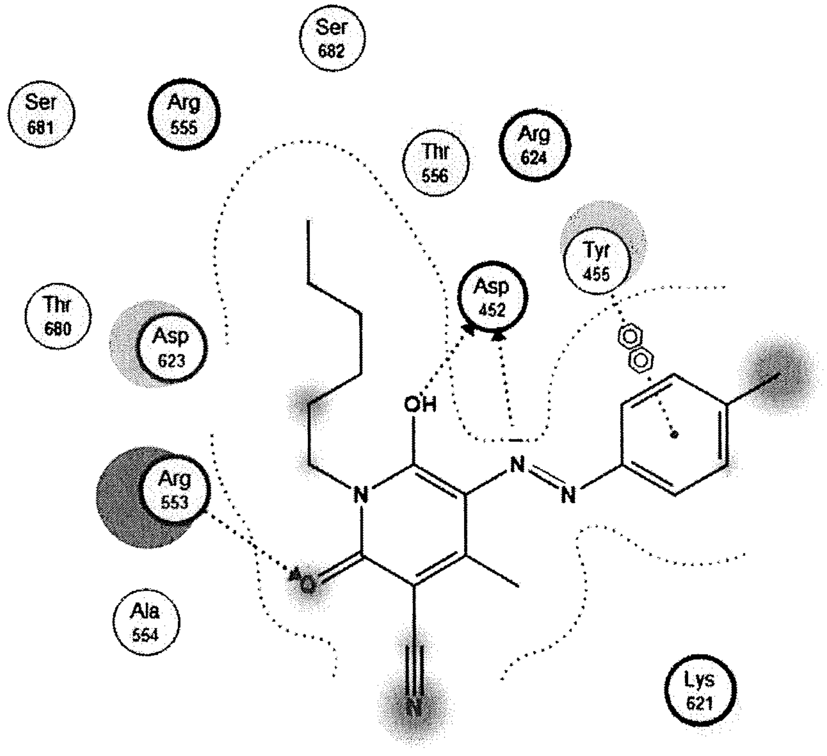
Figure 11D:
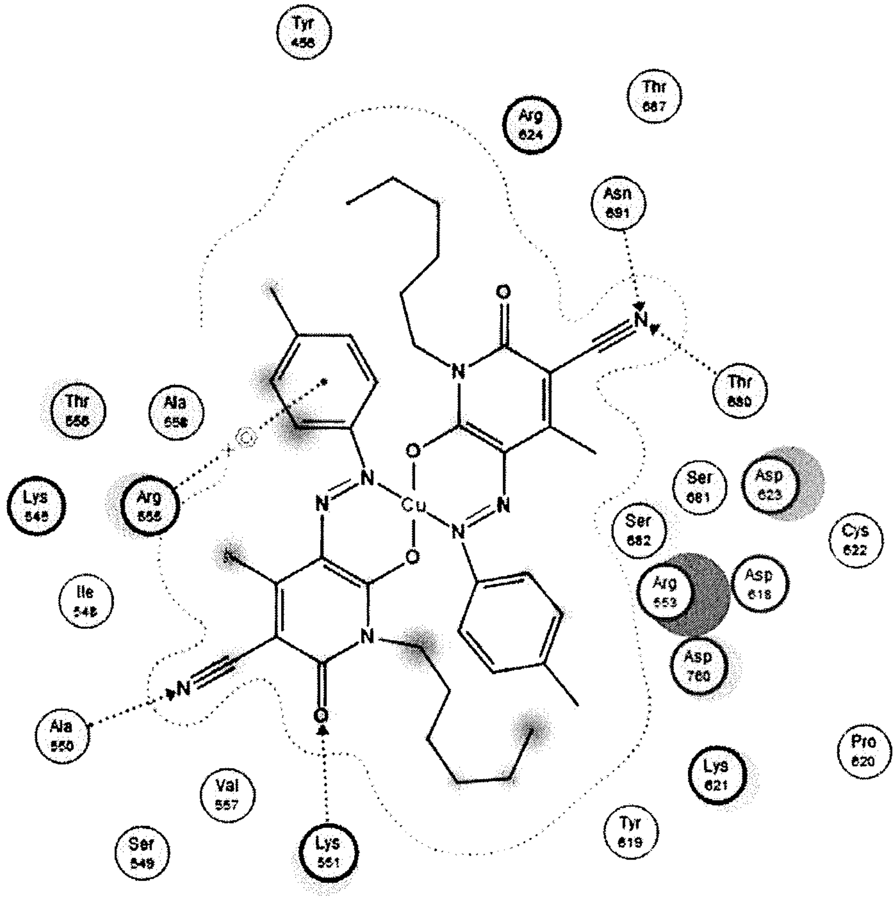

Complex D2=7,7'-dihexyl-10,10'-dimethyl-8,8'-dioxo-3,3'-bis(p-tolyl)-4,4'-spirobi[5-oxa-2,7-diaza-3-azonia-4$\lambda^4$-cuprabicyclo[4.4.0]deca-1(6),2,9-triene]-9,9'-dicarbonitrile In this structure, the Cu-atom is occupying the position at the center of symmetry ($\bar{1}$) and coordinated by four ligands (Table 2). FIG. 4 shows the perspective view of the complex D2 along [111] reflecting the coordination environment of the Cu atom. Two of the ligands are bidentate to the Cu atom through the nitrogen atom of the diazenyl group (N3—N4) and oxygen (O1) atom of the oxidaneyl-group forming the equatorial plane of the octahedral coordination of Cu. The interatomic distances are d(Cu—N4)=2.002(2) Å and d(Cu—O1)=1.930(1) Å, respectively, which are close to the distances reported for azo-azomethine $Cu[C_{22}H_{20}N_3O]_2$and [Cu(agen) complexes]. FIG. 5 shows a packing diagram of D2. Coordination of the central atoms are displayed with octahedra, and intra-15 and intermolecular H-bonding is depicted by dashed lines).

FT-IR Spectra

The FT-IR spectra of the free ligands of (A1, A2) and the respective Cu(II)-complexes (D1, D2) were held in the solid-state to determine the coordination mode of the ligands and complexes, respectively. The stretching vibration of the free ligands v(-OH) at 3434-3460 $cm^{-1}$ was not observed in the IR spectra of the complexes, suggesting the deprotonation of the hydroxyl group and formation of M—O bonds. However, bands between 1617-1626 cm−1 in the free ligands are assigned to v(-CN), and they are shifted to lower wavenumbers in the complexes due to the coordination of the nitrogen atom of the diazenyl to the metal ion. The strong band assigned to v(N═N) at 1511 $cm^{-1}$ in the spectra of free ligands is shifted to higher frequencies in all complexes at 1544 $cm^{-1}$, indicating its involvement in the coordination of the ligands to the metal ions. The bands assignable to v(C≡N) at 2250 $cm^{-1}$ are shifted to lower wavenumber 2216 $cm^{-1}$ in the complex.

Molecular Docking Analysis

Comparing the new Cu(II) complex and their diazenyl pyridinone heterocylic ligands with drugs used for SARS-CoV-2, including Umifenovir, Chloroquine, Camostat, Remdesivir, Ribavirin, Lopinavir showed that the former had strong interactions that were higher than those reported for these drugs. Docking results were calculated with the same protocol. The docking results FIGS. 4-11 and Tables 3-16 represent the high score of the complexes (D1) and (D2) with 2GTB "3CLpro", 5CE1 "PLpro", and 6NUR "RdRp" receptor proteins compared with drugs used in SARS-CoV-2 treatment as known in the prior art or calculated using same protocol. FIGS. 4-11 are as follows: FIG. 4, Perspective view of the molecular structure along [111] reflecting the coordination of the ligands to the central Cu atom; FIG. 5, Packing diagram of D2. Coordination of the central atoms are displayed with octahedra, and intra- and intermolecular H-bonding is depicted by dashed lines; FIG. 6A-D, 3d Docking of the complex D1, D2 and ligand A1, A2 with S-Spike protein receptor 1O86 of SARS-CoV-2. A, Ligand A1; B, Complex D1; C, Ligand A2; D, Complex D2; FIG. 7A-D, 2d Docking of the complex D1, D2 and ligand A1, A2 with S-Spike protein receptor 1O86 of SARS-CoV-2. A, Ligand A1; B, Complex D1; C, Ligand A2; D, Complex D2; FIG. 8A-D, 3d Docking of the complex D1, D2 and ligand A1, A2 with receptor 5CE1 of SARS-CoV-2. A, Ligand A1; B, Complex D1; C, Ligand A2; D, Complex D2; FIG. 9A-D, 2d Docking of the complex D1, D2 and ligand A1, A2 with protein receptor 5CE1 of SARS-CoV-2. A, Ligand A1; B, Complex D1; C, Ligand A2; D, Complex D2; FIG. 10A-D, 3d Docking of the complex D1, D2 and ligand A1, A2 with receptor 6NUR of SARS-CoV-2. A, Ligand A1; B, Complex D1; C, Ligand A2; D, Complex D2; FIG. 11A-C, 2d Docking of the complex D1, D2 and ligand A1, A2 with protein receptor 6NUR of SARS-CoV-2. A, Ligand A1; B, Complex D1; C, Ligand A2; D, Complex D2.

The complex (D2) produced a high docking score toward 1O86 "ACE2" and 4OW0 "PLpro" receptor proteins compared to two ligands and reference drugs.

The high docking score of the complex (D1) toward 2GTB can be attributed to the H-donor interaction of C86 and O115 toward MET165 amino acids of the receptor protein and H-acceptor interaction between O7 and N80 toward GLN 189 in the same receptor protein. The high docking score toward 5CE1 can be explained by stereoselective orientation of the complex D1 and the active site of 5CE1, whereas the high docking score toward 6NUR can be explained by the H-donor interaction between N15 and O of amino acid ASP760 and H-acceptor interactions between N23 and O115 and SER 682.

The high docking score of Complex (D2) toward 1O86 "ACE2" can be attributed to H-donor between N8 and O atom of GLU123, Cu ion to O atom of GLU123 and a π-cation interaction between the 6-membered ring of the complex and the N atom of LYS118. The high score with 4OW0 "PLpro" receptor protein can be explained by the H-acceptor interaction between O43 and O49 toward OH of TYR269 and N of GLN233, and by the π-H interaction between the 6-membered ring of the complex and the carbon atom of MET 209.

TABLE 3

Comparison between the Docking score of the complex D1, D2 and ligand A1, A2 and different SARS-COV-2 receptors

| Compound | 1O86 | 2GTB | 4OW0 | 5CE1 | 6NUR |
|---|---|---|---|---|---|
| Ligand A1 | −8.49 | −7.60 | −8.50 | −7.55 | −7.45 |
| complex D1 | −11.02 | −8.96 | −11.03 | −9.63 | −10.99 |
| ligand A2 | −7.73 | −7.11 | −8.15 | −7.08 | −7.56 |
| complex D2 | −11.21 | −8.56 | −12.20 | −8.19 | −9.56 |

TABLE 4

Reference Docking scores of some drugs used in treatment of SARS-COV-2

| | Binding energy (kcal/mol) | | | | |
|---|---|---|---|---|---|
| Ligand | ACE2 (1O86) | TMPRSS2 (5CE1) | RdRp (6NUR) | 3CLpro (2GTB) | PLpro (4OW0) |
| Arbidol | −4.22 | — | — | — | — |
| Chloroquine | −7.69 | — | — | — | — |
| Camostat mesylate | — | −8.35 | — | — | — |
| Remdesivir | — | — | −4.21 | — | — |
| Ribavirin | — | — | −3.69 | — | — |
| Lopinavir | — | — | — | −9.01 | −4.19 |

TABLE 5

Calculated Docking scores of some prior art drugs used in treatment of SARS-COV-2

| Drug | 1O86 | 2gtb | 4ow0 | 5ce1 | 6NUR |
|---|---|---|---|---|---|
| Umifenovir | −7.26 | −7.23 | −8.31 | −6.88 | −6.54 |
| Chloroquine | −7.1 | −7.03 | −7.83 | −7.28 | −6.82 |
| Camostat | −7.71 | −7.37 | −8.43 | −7.47 | −7.19 |
| Remdesivir | −9.21 | −8.64 | −11.05 | −8.46 | −8.42 |
| Ribavirin | −6.17 | −5.59 | −6.14 | −5.96 | −5.48 |
| Lopinavir | −9.19 | −8.66 | −11.5 | −8.26 | −8.83 |

TABLE 6

Interaction table between complex D1, D2 and ligand A1, A2 with S-Spike protein receptor 1O86 of SARS-COV-2

| z | Ligand | | Receptor | | Interaction | Distance | E (kcal/mol) |
|---|---|---|---|---|---|---|---|
| Ligand A1 | O | 10 | N | GLY 404 (A) | H-acceptor | 3.00 | −1.9 |
| Complex D1 | C | 62 | O | ALA 356 (A) | H-donor | 3.46 | −0.5 |
| | O | 12 | N | ALA 356 (A) | H-acceptor | 2.84 | −1.7 |
| Ligand A2 | N | 6 | OE1 | GLU 403 (A) | H-donor | 2.95 | −4.7 |
| | N | 40 | N | ASP 358 (A) | H-acceptor | 3.54 | −1.6 |
| | C | 24 | 5-ring | HIS 387 (A) | H-pi | 3.74 | −0.7 |
| Complex D2 | N | 8 | OE2 | GLU 123 (A) | H-donor | 2.96 | −0.5 |
| | CU | 1 | OE1 | GLU 123 (A) | Metal | 2.88 | −0.6 |
| | 6-ring | | NZ | LYS 118 (A) | pi-cation | 3.46 | −0.5 |

TABLE 7

Docking score and energy of the complex D1, D2 and ligand A1, A2 with S-Spike protein receptor 1O86 of SARS-CoV-2

| Compound | S | rmsd_refine | E_conf | E_place | E_refine | E_score2 |
|---|---|---|---|---|---|---|
| Ligand A1 | −8.49 | 4.59 | 28.72 | −74.78 | −46.60 | −8.49 |
| | −7.96 | 1.61 | 31.46 | −60.72 | −46.37 | −7.96 |
| | −7.61 | 1.30 | 33.64 | −94.35 | −42.32 | −7.61 |
| | −7.50 | 1.34 | 29.99 | −89.46 | −40.33 | −7.50 |
| | −7.43 | 2.58 | 24.95 | −72.64 | −40.03 | −7.43 |
| Complex D1 | −11.02 | 2.31 | −23.55 | −83.11 | −63.62 | −11.02 |
| | −10.75 | 2.05 | −34.11 | −117.39 | −64.55 | −10.75 |
| | −10.49 | 1.46 | −38.00 | −83.02 | −63.77 | −10.49 |
| | −10.46 | 1.88 | −21.12 | −94.70 | −49.30 | −10.46 |
| | −10.44 | 1.58 | −26.89 | −100.49 | −54.37 | −10.44 |
| Ligand A2 | −7.73 | 1.54 | −12.89 | −53.26 | −33.74 | −7.73 |
| | −7.59 | 2.99 | −6.57 | −55.67 | −40.15 | −7.59 |
| | −7.31 | 1.64 | −8.14 | −84.54 | −40.33 | −7.31 |
| | −7.26 | 1.27 | −14.29 | −102.17 | −40.97 | −7.26 |
| | −7.24 | 1.89 | −3.75 | −69.67 | −35.79 | −7.24 |
| complex D2 | −11.21 | 3.20 | 19.78 | −103.46 | −64.08 | −11.21 |
| | −10.58 | 2.21 | 8.36 | −68.30 | −58.81 | −10.58 |
| | −10.18 | 2.33 | 29.89 | −33.44 | −56.48 | −10.18 |
| | −10.17 | 2.70 | 13.20 | −82.11 | −61.76 | −10.17 |
| | −9.75 | 1.49 | 20.62 | −49.19 | −59.64 | −9.75 |

TABLE 8

Interaction table between the complex D1, D2 and ligand A1, A2 with protein receptor 5CE1 of SARS-COV-2

| z | Ligand | Receptor | | | | Interaction | Distance | E (kcal/mol) |
|---|---|---|---|---|---|---|---|---|
| Ligand A1 | O 6 | N | GLY | 378 | (A) | H-acceptor | 3.16 | −3.9 |
| Complex D1 | No measurable interactions | | | | | | | |
| Ligand A2 | N 3 | OG | SER | 353 | (A) | H-donor | 3.16 | −0.7 |
| Complex D2 | 6-ring | CB | HIS | 203 | (A) | pi-H | 4.28 | −0.6 |

TABLE 9

Docking score and energy of the complex D1, D2 and ligand A1, A2 with protein receptor 5CE1 of SARS-CoV-2

| mseq | S | rmsd_refine | E_conf | E_place | E_refine | E_score2 |
|---|---|---|---|---|---|---|
| Ligand | −7.55 | 1.23 | 21.31 | −67.02 | −42.88 | −7.55 |
| A1 | −7.52 | 2.08 | 33.67 | −74.06 | −44.02 | −7.52 |
| | −7.34 | 1.94 | 20.16 | −68.58 | −40.55 | −7.34 |
| | −7.33 | 1.41 | 20.46 | −68.02 | −44.00 | −7.33 |
| | −7.32 | 1.97 | 25.85 | −77.09 | −44.19 | −7.32 |
| Complex | −9.63 | 1.73 | −36.83 | −72.86 | −60.51 | −9.63 |
| D1 | −9.40 | 2.07 | −26.46 | −60.85 | −57.72 | −9.40 |
| | −9.08 | 2.17 | 36.17 | −70.39 | −55.37 | −9.08 |
| | −8.77 | 2.32 | −28.98 | −70.71 | −49.22 | −8.77 |
| | −8.56 | 2.48 | −29.29 | −58.23 | −47.64 | −8.56 |
| Ligand | −7.08 | 1.49 | −14.94 | −72.35 | −41.87 | −7.08 |
| A2 | −7.00 | 1.52 | −4.79 | −57.11 | −42.69 | −7.00 |
| | −6.90 | 1.24 | −16.89 | −84.98 | −37.96 | −6.90 |
| | −6.84 | 3.35 | −15.98 | −56.02 | −38.52 | −6.84 |
| | −6.74 | 1.58 | −3.74 | −68.47 | −36.01 | −6.74 |
| Complex | −8.19 | 2.91 | 20.10 | −64.19 | −47.63 | −8.19 |
| D2 | −8.16 | 2.66 | 4.78 | −19.27 | −51.31 | −8.16 |
| | −8.06 | 2.30 | 17.11 | −50.18 | −44.95 | −8.06 |
| | −7.94 | 2.50 | 8.22 | −41.20 | −50.55 | −7.94 |
| | −7.89 | 1.79 | 13.82 | −44.64 | −44.59 | −7.89 |

TABLE 10

Interaction table between the complex D1, D2 and ligand A1, A2 with protein receptor 6NUR of SARS-COV-2

| z | Ligand | | Receptor | | | | Interaction | Distance | E (kcal/mol) |
|---|---|---|---|---|---|---|---|---|---|
| Ligand | O | 1 | NH2 | ARG | 624 | (A) | H-acceptor | 2.93 | −0.6 |
| A1 | O | 6 | NH1 | ARG | 553 | (A) | H-acceptor | 3.15 | −3.3 |
| | N | 17 | NZ | LYS | 545 | (A) | H-acceptor | 3.39 | −4.8 |
| | N | 17 | NE | ARG | 555 | (A) | H-acceptor | 3.35 | −2.4 |
| | N | 17 | NH2 | ARG | 555 | (A) | H-acceptor | 3.13 | −4.8 |
| | 6-ring | | N | THR | 556 | (A) | pi-H | 4.02 | −1.6 |
| Complex | N | 15 | OD2 | ASP | 760 | (A) | H-donor | 3.31 | −2.6 |
| D1 | N | 23 | NH2 | ARG | 555 | (A) | H-acceptor | 3.14 | −3.3 |
| | O | 115 | N | SER | 682 | (A) | H-acceptor | 3.02 | −1.2 |
| | O | 115 | OG | SER | 682 | (A) | H-acceptor | 3.10 | −0.9 |
| Ligand | O | 1 | OD1 | ASP | 452 | (A) | H-donor | 2.91 | −5.8 |
| A2 | N | 6 | OD1 | ASP | 452 | (A) | H-donor | 3.20 | −2.9 |
| | O | 25 | NH2 | ARG | 553 | (A) | H-acceptor | 3.26 | −0.8 |
| | 6-ring | | 6-ring | TYR | 455 | (A) | pi-pi | 3.57 | −0.0 |
| Complex | O | 49 | NZ | LYS | 551 | (A) | H-acceptor | 3.39 | −2.2 |
| D2 | N | 73 | OG1 | THR | 680 | (A) | H-acceptor | 2.82 | −2.4 |
| | N | 73 | ND2 | ASN | 691 | (A) | H-acceptor | 2.93 | −4.3 |
| | N | 77 | N | ALA | 550 | (A) | H-acceptor | 3.14 | −3.3 |
| | 6-ring | | NH2 | ARG | 555 | (A) | pi-cation | 3.84 | −1.1 |

TABLE 11

Docking score and energy of the complex D1, D2 and ligand A1, A2 with protein receptor 6NUR of SARS-CoV-2

| mseq | S | rmsd_refine | E_conf | E_place | E_refine | E_score2 |
|---|---|---|---|---|---|---|
| Ligand | −7.45 | 2.00 | 22.72 | −102.46 | −39.17 | −7.45 |
| A1 | −7.40 | 1.47 | 25.91 | −80.05 | −39.49 | −7.40 |
| | −7.17 | 1.71 | 32.22 | −65.25 | −30.00 | −7.17 |
| | −7.17 | 1.38 | 26.77 | −94.75 | −40.69 | −7.17 |
| | −7.00 | 1.80 | 34.95 | −85.20 | −38.60 | −7.00 |
| Complex | −10.99 | 2.14 | −21.69 | −93.35 | −71.37 | −10.99 |
| D1 | −10.17 | 1.79 | −30.85 | −81.57 | −62.09 | −10.17 |
| | −9.84 | 3.87 | −27.22 | −90.94 | −64.79 | −9.84 |
| | −9.71 | 1.76 | −23.53 | −76.27 | −51.35 | −9.71 |
| | −9.61 | 1.46 | −36.66 | −68.05 | −61.36 | −9.61 |
| Ligand | −7.56 | 1.69 | −2.90 | −80.85 | −43.49 | −7.56 |
| A2 | −7.03 | 1.60 | −7.55 | −59.57 | −28.89 | −7.03 |
| | −6.90 | 1.26 | −1.37 | −89.61 | −29.93 | −6.90 |
| | −6.77 | 3.40 | −16.76 | −67.94 | −39.73 | −6.77 |
| | −6.72 | 1.67 | 0.08 | −92.11 | −38.37 | −6.72 |
| complex | −9.56 | 1.55 | 17.97 | −104.68 | −54.30 | −9.56 |
| D2 | −9.06 | 1.07 | 13.06 | −108.75 | −52.81 | −9.06 |
| | −8.66 | 1.73 | 9.22 | −87.30 | −46.07 | −8.66 |
| | −8.65 | 2.63 | 7.60 | −81.08 | −49.08 | −8.65 |
| | −8.54 | 1.85 | 7.11 | −70.79 | −47.67 | −8.54 |

TABLE 12

Docking score and energy of the compounds and 1O86 protein

| comp. | S | rmsd_refine | E_conf | E_place | E_score1 | E_refine | E_score2 |
|---|---|---|---|---|---|---|---|
| Umifenovir | −7.26 | 1.33 | 65.41 | −93.92 | −10.48 | −41.11 | −7.26 |
| Chloroquine | −7.10 | 1.64 | −45.50 | −65.54 | −9.39 | −37.52 | −7.10 |
| Camostat | −7.71 | 1.80 | −116.94 | −78.17 | −9.95 | −34.14 | −7.71 |
| Remdesivir | −9.21 | 1.59 | −29.39 | −114.79 | −9.90 | −56.98 | −9.21 |
| Ribavirin | −6.17 | 1.16 | 149.11 | −71.88 | −11.60 | −24.89 | −6.17 |
| Lopinavir | −9.19 | 2.47 | −59.70 | −51.38 | −9.40 | −54.28 | −9.19 |

TABLE 13

| Docking score and energy of the compounds and 2gtb protein | | | | | | | |
|---|---|---|---|---|---|---|---|
| comp. | S | rmsd_refine | E_conf | E_place | E_score1 | E_refine | E_score2 |
| Umifenovir | −7.23 | 2.36 | 72.87 | −63.18 | −10.11 | −37.59 | −7.23 |
| Chloroquine | −7.03 | 1.69 | −26.96 | −52.10 | −9.48 | −32.28 | −7.03 |
| Camostat | −7.37 | 1.90 | −121.50 | −62.62 | −9.67 | −42.81 | −7.37 |
| Remdesivir | −8.64 | 1.39 | −43.66 | −89.43 | −9.74 | −47.34 | −8.64 |
| Ribavirin | −5.59 | 1.28 | 154.07 | −75.52 | −9.82 | −25.79 | −5.59 |
| Lopinavir | −8.66 | 1.81 | −60.54 | −53.88 | −8.62 | −50.98 | −8.66 |

TABLE 14

| Docking score and energy of the compounds and 4ow0 protein | | | | | | | |
|---|---|---|---|---|---|---|---|
| comp. | S | rmsd_refine | E_conf | E_place | E_score1 | E refine | E_score2 |
| Umifenovir | −8.31 | 3.61 | 66.94 | −93.12 | −10.71 | −51.37 | −8.31 |
| Chloroquine | −7.83 | 2.09 | −44.03 | −59.46 | −9.80 | −40.10 | −7.83 |
| Camostat | −8.43 | 1.71 | −120.22 | −80.50 | −10.85 | −41.53 | −8.43 |
| Remdesivir | −11.05 | 2.02 | −34.05 | −90.49 | −10.39 | −63.67 | −11.05 |
| Ribavirin | −6.14 | 1.95 | 150.94 | −87.71 | −10.41 | −29.69 | −6.14 |
| Lopinavir | −11.50 | 2.00 | −38.70 | −104.83 | −10.82 | −61.13 | −11.50 |

TABLE 15

| Docking score and energy of the compounds and 5ce1 protein | | | | | | | |
|---|---|---|---|---|---|---|---|
| comp. | S | rmsd_refine | E_conf | E_place | E_score1 | E_refine | E_score2 |
| Umifenovir | −6.88 | 2.06 | 70.21 | −50.29 | −9.66 | −39.44 | −6.88 |
| Chloroquine | −7.28 | 1.82 | −38.19 | −62.48 | −9.21 | −35.43 | −7.28 |
| Camostat | −7.47 | 1.79 | −120.35 | −62.38 | −10.36 | −37.85 | −7.47 |
| Remdesivir | −8.46 | 2.09 | −28.96 | −52.64 | −10.44 | −51.84 | −8.46 |
| Ribavirin | −5.96 | 1.00 | 152.47 | −64.15 | −9.68 | −34.52 | −5.96 |
| Lopinavir | −8.26 | 1.81 | −67.22 | −76.21 | −9.74 | −50.19 | −8.26 |

TABLE 16

| Interaction table between the compounds and 6nur protein | | | | | | | |
|---|---|---|---|---|---|---|---|
| comp. | S | rmsd_refine | E_conf | E_place | E_score1 | E_refine | E_score2 |
| Umifenovir | −6.54 | 2.05 | 64.49 | −50.30 | −9.62 | −36.26 | −6.54 |
| Chloroquine | −6.82 | 3.10 | −43.44 | −54.45 | −8.96 | −32.20 | −6.82 |
| Camostat | −7.19 | 1.97 | −121.40 | −70.96 | −11.20 | −40.19 | −7.19 |
| Remdesivir | −8.42 | 2.60 | −46.00 | −85.37 | −10.72 | −50.77 | −8.42 |
| Ribavirin | −5.48 | 1.23 | 150.97 | −72.87 | −12.19 | −12.27 | −5.48 |
| Lopinavir | −8.83 | 1.59 | −49.27 | −30.42 | −9.80 | −42.16 | −8.83 |

Summary for Example 2

Advantages of the present invention include introducing the therapeutic inhibition affinity of copper(II) complexes to inhibit the infection process of SARS-CoV-2. This is supported with docking results of the Cu(II) complexes and their diazenyl pyridinone heterocyclic ligands. Comparing the present Cu(II) complexes and their diazenyl pyridinone heterocylic ligands with drugs used for SARS-CoV-2, including Umifenovir, Chloroquine, Camostat, Remdesivir, Ribavirin, Lopinavir, revealed strong interactions on the part of the Cu(II) complexes. Docking results were calculated with the same protocol. Choosing the chain that binds with the appropriate native ligand was determined by the coordinates of the space (pocket cavity) of the ligand. The proteins that were targeted included ACE2, TMPRSS 2, RdRP, 3CLpro and PLpro. The materials used in conducting this research were sample structures of the target proteins, namely ACE2 (PDB ID: 1O86), TMPRSS2 (PDB ID: 5CE1), RdRp (PDB ID: 6NUR), 3CLpro (PDB ID: 2GTB) and PLpro (PDB ID: PDB ID:4OW0) downloaded from the website located at rcsb.org.

Example 3. In Vitro Studies

Inhibitory and Cytotoxicity Effect

Methodology

1. MTT Cytotoxicity Assay

To assess the half maximal cytotoxic concentration ($CC_{50}$), stock solutions of the test compounds were prepared in 10% DMSO in $ddH_2O$ and diluted further to the working solutions with DMEM. The cytotoxic activity of the extracts was tested in VERO-E6 cells by using the 3-(4,5-dimethylthiazol-2-yl)-2,5-diphenyltetrazolium bromide (MTT) method with minor modifications. Briefly, the cells were seeded in 96 well-plates (100 μl/well at a density of 3×105 cells/ml) and incubated for 24 h at 37° C. in 5% $CO_2$. After 24 h, cells were treated with various concentrations of the tested compounds in triplicates. 24 h later, the supernatant was discarded, and cell monolayers were washed with sterile 1× phosphate buffer saline (PBS) 3 times and MTT solution (20 μl of 5 mg/ml stock solution) was add to each well and incubated at 37° C. for 4 h followed by medium aspiration. In each well, the formed formazan crystals were dissolved with 200 μl of acidified isopropanol (0.04 M HCl in absolute isopropanol=0.073 ml HCL in 50 ml isopropanol). Absorbance of formazan solutions was measured at λ max 540 nm with 620 nm as a reference wavelength using a multi-well plate reader. The percentage of cytotoxicity compared to the untreated cells was determined with the following equation.

% cytotoxicity=((absorbance of cells without treatment−absorbance of cells with treatment)×100)/(absorbance of cells without treatment)

2. Inhibitory Concentration 50 ($IC_{50}$) Determination

In 96-well tissue culture plates, 2.4×104 Vero-E6 cells were distributed in each well and incubated overnight in a humidified 37° C. incubator under 5% $CO_2$. The cell monolayers were then washed once with 1×PBS and subjected to virus adsorption (hCoV-19/Egypt/NRC-03/2020 (Accession Number on GSAID: EPI_ISL_430820)) for 1 h at room temperature (RT). The cell monolayers were further overlaid with 100 μl of DMEM containing varying concentrations of the test compounds. Following incubation at 37° C. in 5% $CO_2$ incubator for 72 h, the cells were fixed with 100 μl of 4% paraformaldehyde for 20 min and stained with 0.1% crystal violet in distilled water for 15 min at RT. The crystal violet dye was then dissolved using 100 μl absolute methanol per well and the optical density of the color was measured at 570 nm using Anthos Zenyth 200rt plate reader (Anthos Labtec Instruments, Heerhugowaard, Netherlands). The $IC_{50}$ of the compound is that required to reduce the virus-induced cytopathic effect (CPE) by 50%, relative to the virus control.

3. Results

Figure 12:
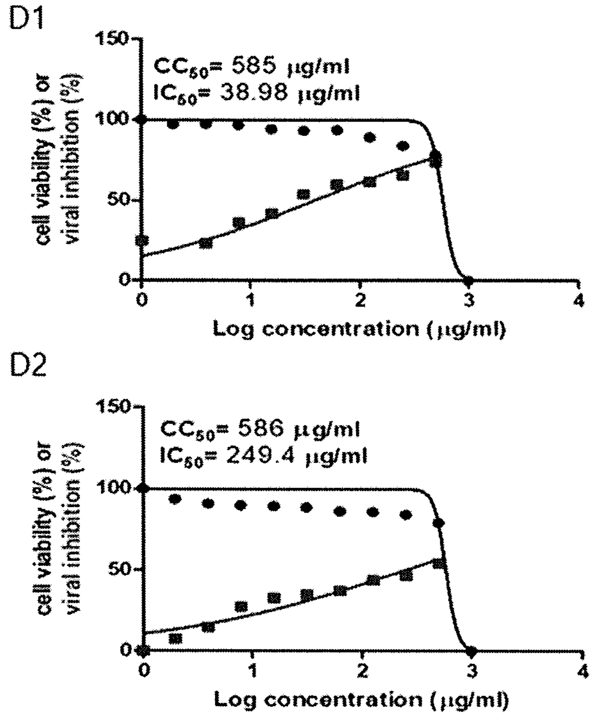
FIG. 12. Graph of Cytotoxicity concentration 50 ($CC_{50}$) and Inhibitory concentration 50 ($IC_{50}$) of complexes D1, D2 and ligands A1, A2 with S-Spike protein receptor 1O86 of SARS-CoV-2.

The tested products with D1 and D2 code showed an active antiviral activity against SARS-CoV-2 respectively as shown in FIG. 12.

4. Conclusion

In agreement with the results of the theoretical docking calculations, D1 and D2 exhibited significant antiviral activity. D1 had a somewhat higher inhibitory effect compared to D2, but both of them exhibited an acceptable range of viral inhibition and low toxicity.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A method of preventing or treating a SARS-CoV-2 infection in a subject in need thereof, comprising administering to the subject a therapeutically effective compound of Formula I:

Formula I

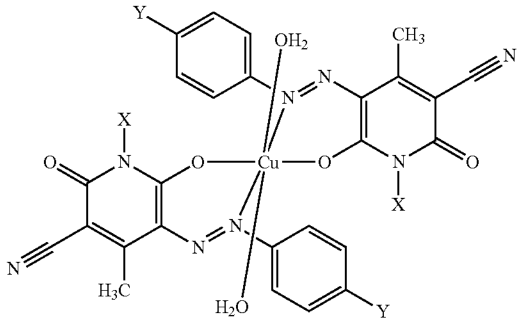

where Y is $NO_2$ or $CH_3$ and X=butyl, hexyl or benzyl.

2. The method of claim 1, wherein the compound is

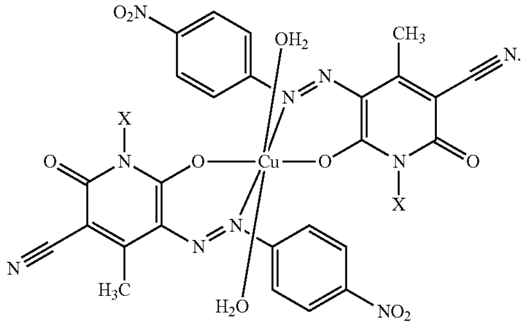

3. The method of claim 1, wherein the compound is

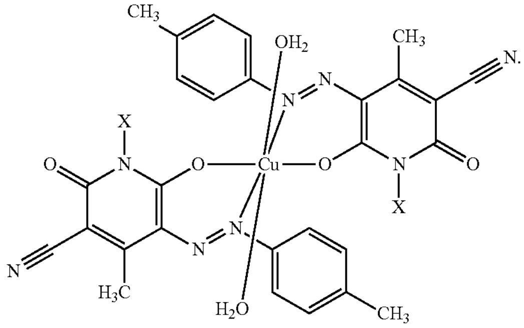

4. The method of claim 1, wherein the compound is

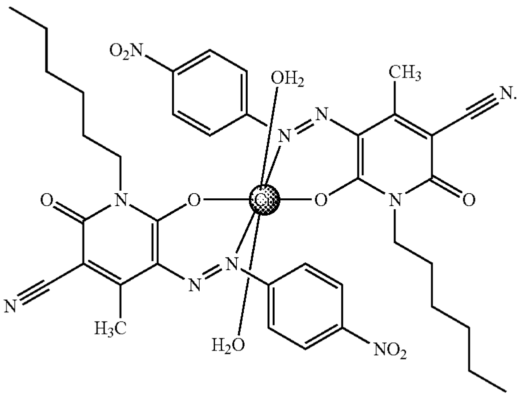

5. The method of claim 1, wherein the compound is

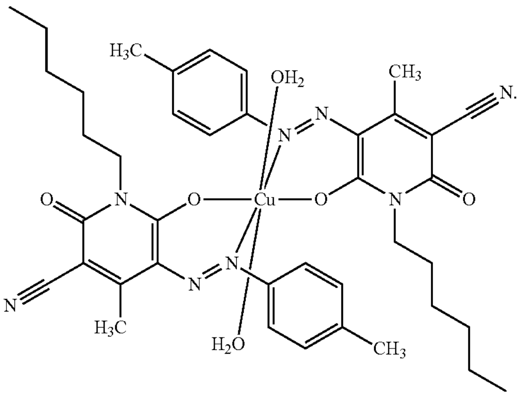

6. A method of preventing a SARS-CoV-2 virus from infecting a host cell, comprising contacting i) one or more viral proteins of the SARS-CoV-2 virus and/or ii) one or more surface receptor proteins of the host cell, with a compound of Formula I:

Formula I

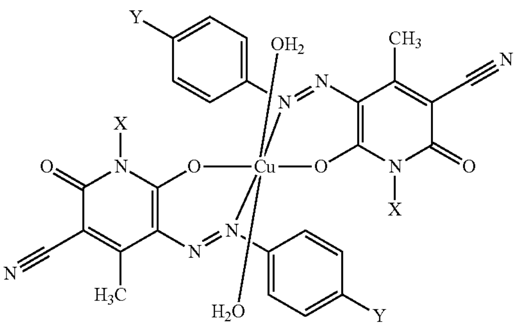

where Y is $NO_2$ or $CH_3$ and X=butyl, hexyl or benzyl.

7. The method of claim 6, wherein the compound is

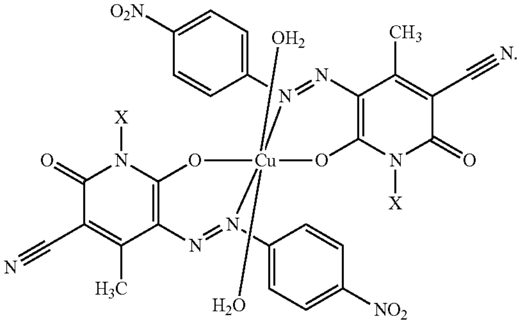

8. The method of claim 6, wherein the compound is

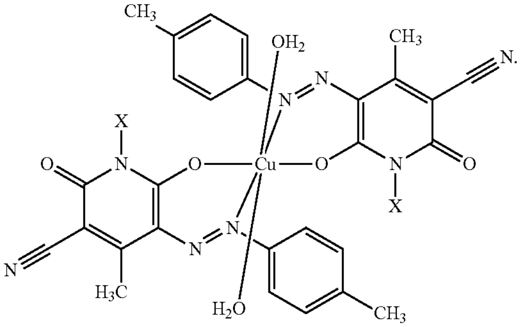

9. The method of claim 6, wherein the compound is

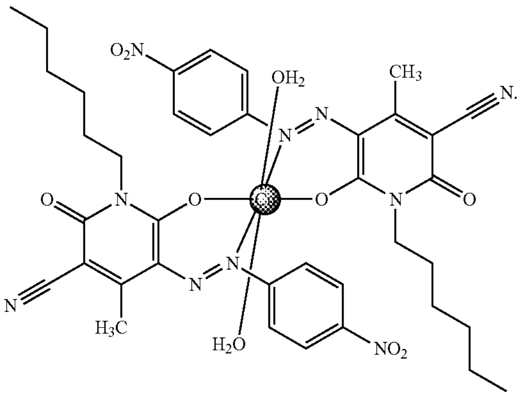

10. The method of claim 6, wherein the compound is
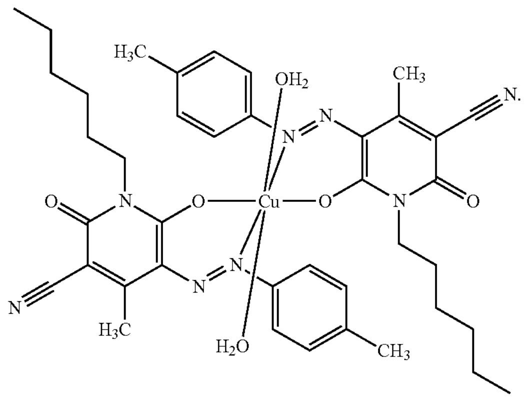
* * * * *